United States Patent
Kuhn et al.

(10) Patent No.: US 10,417,804 B2
(45) Date of Patent: Sep. 17, 2019

(54) SYSTEM AND METHOD FOR THREE-DIMENSIONAL PRINTING, HOLOGRAPHIC AND VIRTUAL REALITY RENDERING FROM MEDICAL IMAGE PROCESSING

(71) Applicant: TeraRecon, Inc., Foster City, CA (US)

(72) Inventors: Gael Kuhn, FR (FR); Tiecheng Zhao, Concord, CA (US); David J. G. Guigonis, Union City, CA (US); Jeffrey L. Sorenson, Wake Forest, NC (US); David W. MacCutcheon, Marshfield, MA (US)

(73) Assignee: TeraRecon, Inc., Foster City, CA (US)

( * ) Notice: Subject to any disclaimer, the term of this patent is extended or adjusted under 35 U.S.C. 154(b) by 0 days.

(21) Appl. No.: 16/360,363

(22) Filed: Mar. 21, 2019

(65) Prior Publication Data

US 2019/0221025 A1 Jul. 18, 2019

Related U.S. Application Data

(63) Continuation of application No. 15/812,912, filed on Nov. 14, 2017, now Pat. No. 10,275,927.

(Continued)

(51) Int. Cl.
*G06T 15/00* (2011.01)
*G06T 7/00* (2017.01)
(Continued)

(52) U.S. Cl.
CPC ............ *G06T 15/005* (2013.01); *B33Y 50/00* (2014.12); *G06T 7/0012* (2013.01); *G06T 7/11* (2017.01); *G06T 15/00* (2013.01); *G06T 19/00* (2013.01); *G06T 19/006* (2013.01); *G06T 19/20* (2013.01); *G16H 30/20* (2018.01); *G06T 2200/04* (2013.01); *G06T 2200/24* (2013.01);

(Continued)

(58) Field of Classification Search
None
See application file for complete search history.

(56) References Cited

U.S. PATENT DOCUMENTS

2016/0225192 A1* 8/2016 Jones ...................... G06F 3/012

OTHER PUBLICATIONS

Park et al., Mobile Collaborative Medical Display System, Computer Methods and Programs in Biomedicine, Dec. 2008, 248-260 (Year: 2008).*

* cited by examiner

*Primary Examiner* — Robert J Craddock
(74) *Attorney, Agent, or Firm* — Douglas L. Weller

(57) ABSTRACT

Multiple person viewing of rendered medical image is achieved by manipulating an image by the server to produce first rendered medical image data that includes the medical image data plus image manipulation results. A first 3-D medical image that is based on the first rendered medical image data is displayed within an augmented reality environment or a virtual reality environment so that the first end user has a first viewer location and a first viewing angle of the first 3-D medical image. A second 3-D medical image that is based on second rendered medical image data is displayed within the augmented reality environment or the virtual reality environment so that the second end user has at least one of a second viewer location and a second viewing angle that is different from at least one of the first viewer location and the first viewing angle of the first 3-D medical image.

20 Claims, 26 Drawing Sheets

Related U.S. Application Data

(60) Provisional application No. 62/424,933, filed on Nov. 21, 2016, provisional application No. 62/423,143, filed on Nov. 16, 2016.

(51) Int. Cl.
| | |
|---|---|
| *G06T 19/00* | (2011.01) |
| *B33Y 50/00* | (2015.01) |
| *G16H 30/20* | (2018.01) |
| *G06T 19/20* | (2011.01) |
| *G06T 7/11* | (2017.01) |
| *G16H 30/40* | (2018.01) |
| *H04L 29/08* | (2006.01) |

(52) U.S. Cl.
CPC .... *G06T 2207/30048* (2013.01); *G16H 30/40* (2018.01); *H04L 67/10* (2013.01)

| Anonymize Setup | | | |
|---|---|---|---|
| [Group Element] | Title | Original Value | Replacement Value |
| (0008,0020) | Study Date | 19980504 | 19980504 |
| (0008,1030) | Study Description | AAA PROTOCOL | Brain MRI (DWI-PWI) |
| (0010,0010) | Patient's Name | AAA | ValueNotSet |
| (0010,0020) | Patient ID | MDCT_4 | ValueNotSet |
| (0010,0030) | Patient's Birth Date | ValueNotAvailable | ValueNotSet |
| (0010,1000) | Other Patient IDs | ValueNotAvailable | ValueNotSet |
| (0020,0010) | Study ID | 318 | CAIN1 |
| 1101 | 1102 | 1103 | 1104 |

Static

OK    Abort

1100

FIG. 7 ered medical images in accordance
SYSTEM AND METHOD FOR THREE-DIMENSIONAL PRINTING, HOLOGRAPHIC AND VIRTUAL REALITY RENDERING FROM MEDICAL IMAGE PROCESSING

RELATED APPLICATIONS

This application is a continuation of U.S. application Ser. No. 15/821,912 filed Nov. 14, 2017, which claims the benefit of U.S. Provisional Application No. 62/423,143 filed Nov. 16, 2016 and U.S. Provisional Application No. 62/424,933 filed Nov. 21, 2016. The disclosures of the above applications are incorporated by reference herein in their entirety.

BACKGROUND

Field of the Invention

Embodiments of the present invention relate generally to medical information processing systems. More particularly, embodiments of the invention relate to three-dimensional printing, holographic and virtual reality rendering from medical image processing.

Background

Three-dimensional (3D) printing allows for the production of three dimensional solid objects from a digital file. In a layering process, one layer is added after the other until a fully formed object is produced. 3D printing has many medical uses. For example, 3D printed models of cancerous tumors have been used in anti-cancer drugs and when researching how tumors develop, grow, and spread.

3D printing has also been used for tissue engineering. For example, research has been conducted about 3-D printer use in replacing blood vessels, binding chemicals to bones, manufacturing heart valves, replicating human ears, creating synthetic kin, creating synthetic organs and printing drugs.

BRIEF DESCRIPTION OF DRAWINGS

FIG. 6, FIG. 7 and FIG. 8 illustrate use of a graphics user interface illustrate application of color to a module and the embedding of a color palette into a file ready for exchange between entities in a network.

DETAILED DESCRIPTION

Figure 1:
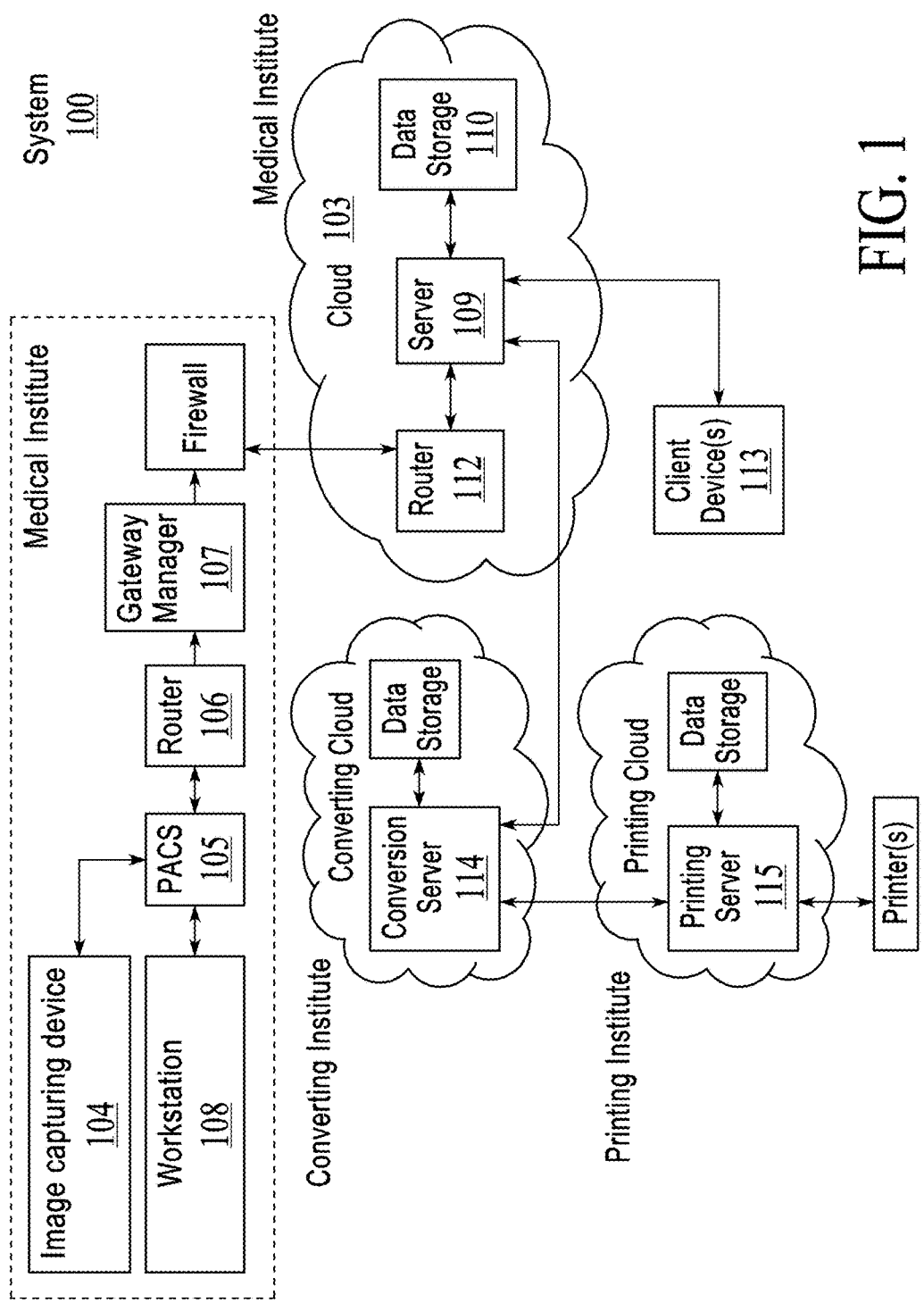
FIG. 1 is a simplified block diagram illustrating a network that allows for printing applications in a medical environment.

FIG. 1 is a block diagram illustrating a cloud-based image processing system with three-dimensional (3D) Printing (referred to as 3D Printing System) of medical imaging in accordance with an embodiment. FIG. 1 shows a system 100 that includes one or more entities or institutes communicatively coupled to one or more cloud systems over a network. Entities may represent a variety of organizations such as medical institutes having a variety of facilities residing all over the world. Entities may represent a variety of organizations such as medical institutes, file conversion institutes, printing institutes, or any combination thereof having a variety of facilities residing all over the world. For example, entity may include or be associated with image capturing device or devices 104, image storage system (e.g., PACS) 105, router 106, and/or data gateway manager 107. Image storage system 105 may be maintained by a third-party entity that provides archiving services to entity 101, which may be accessed by workstation 108 such as an administrator or user associated with entity 101. Note that throughout this application, a medical institute is utilized as an example of an organization entity. However, it is not so limited; other organizations or entities may also be applied such as a printing entity and/or a file conversion entity.

In one embodiment, cloud 103 may represent a set of servers or clusters of servers associated with one or more service provider and geographically distributed over a network. For example, cloud 103 may be associated with a medical image processing service provider such as TeraRecon of Foster City, Calif. For example, cloud 103 may be associated with a medical image processing service provider such as TeraRecon of Foster City, Calif., a printing service provider, a file conversion service provider, or any combination thereof (not shown). The printing task can be externalized through a 3D printing service or can be locally-sited if the entity has its own printing capabilities. In the case of locally-sited printing capabilities, the conversion service (which can be cloud based or locally sited) will provide a print ready file in a format supported by the 3D printer. A network may be a local area network (LAN), a metropolitan area network (MAN), a wide area network (WAN) such as the Internet or an intranet, or a combination thereof. Cloud 103 can be made of a variety of servers and devices capable of providing application services to a variety of clients 113 (e.g., a tablet computing device, a mobile device, a desktop, a laptop, or any combination thereof) over a network. In one embodiment, cloud 103 includes one or more cloud servers 109 to provide image processing services, one or more databases 110 to store images and other medical data, and one or more routers 112 to transfer data to/from other entities. If the cloud server consists of a server cluster, or more than one server, rules may exist which control the transfer of data between the servers in the cluster. For example, there may be reasons why data on a server in one country should not be placed on a server in another country.

Server 109 may be an image processing server to provide medical image processing services to clients 113 over a network. For example, server 109 may be implemented as part of an iNtuition server, TeraRecon AquariusNET™ server and/or a TeraRecon AquariusAPS server. Users can manipulate images on the client device 113 which can transmit the request to server 109 to perform the image processing. Data gateway manager 107 and/or router 106 may be implemented as part of a TeraRecon AquariusGATE device. Medical imaging device 104 may be an image diagnosis device, such as angio, X-ray, CT device, MRI scanning device, nuclear medicine device, ultrasound device, or any other medical imaging device. Medical imaging device 104 collects information from multiple cross-section views of a specimen, reconstructs them, and produces medical image data for the multiple cross-section views. Medical imaging device 104 is also referred to as a modality.

Database 110 may be a data store to store medical data such as digital imaging and communications in medicine (DICOM) compatible data or other image data. Database 110 may also incorporate encryption capabilities. Database 110 may include multiple databases and/or may be maintained by a third-party vendor such as storage providers. Data store 110 may be implemented with relational database management systems (RDBMS), e.g., Oracle™ database or Microsoft® SQL Server, etc. Clients 113 may represent a variety of client devices such as a desktop, laptop, tablet computing device, mobile phone, personal digital assistant (PDA), etc. Some of clients 113 may include a client application (e.g., thin client application) to access resources such as medical image processing tools or applications hosted by server 109 over a network. Examples of thin clients include a web browser, a phone application and others. Client applications can have an option to print over a network.

According to one embodiment, server 109 is configured to provide advanced image processing services to clients 113, which may represent physicians from medical institutes, agents from insurance companies, patients, medical researchers, etc. Cloud server 109, also referred to as an image processing server, has the capability of hosting one or more medical images and data associated with the medical images to allow multiple participants such as clients 113, to participate in a discussion/processing forum of the images in a collaborated manner or conferencing environment. Different participants may participate in different stages and/or levels of a discussion session or a workflow process of the images. Dependent upon the privileges associated with their roles (e.g., doctors, insurance agents, patients, or third-party data analysts or researchers), different participants may be limited to access only a portion of the information relating to the images or a subset of the tools and functions without compromising the privacy of the patients associated with the images. Dependent upon the privileges associated with their roles, different participants can manipulate, mask, and/or color the image. Server 109 can anonymize and/or de-identify any data files to remove any Protected Health Information.

According to some embodiments, data gateway manager 107 is configured to automatically or manually transfer medical data to/from data providers (e.g., PACS systems) such as medical institutes. Such data gateway management may be performed based on a set of rules or policies, which may be configured by an administrator or some other authorized personnel. In one embodiment, in response to updates of medical images data during an image discussion session or image processing operations performed in the cloud, the data gateway manager is configured to transmit over a network (e.g., Internet) the updated image data or the difference between the updated image data and the original image data to a data provider such as PACS 105 that provided the original medical image data. Similarly, data gateway manager 107 can be configured to transmit any new images and/or image data from the data provider, where the new images may have been captured by an image capturing device such as image capturing device 104 associated with entity 101. In addition, data gateway manager 107 may further transfer data amongst multiple data providers that is associated with the same entity (e.g., multiple facilities of a medical institute). Furthermore, cloud 103 may include an advanced preprocessing system (not shown) to automatically perform certain pre-processing operations of the received images using certain advanced image processing resources provided by the cloud systems. For example, preprocessing system can preprocess the image to enable the user to start modeling with predefined models such as bone removal (i.e., the image can be preprocessed to remove bone such that the user can view the image without bone). In one embodiment, gateway manager 107 is configured to communicate with cloud 103 via certain Internet ports. The data being transferred may be encrypted and/or compressed using a variety of encryption and compression methods. The term "Internet port" in this context could also be an intranet port, or a private port on an intranet.

In one embodiment, converting cloud may represent a set of servers or clusters of servers associated with one or more service provider and geographically distributed over a network. For example, converting cloud may be associated with a file converting service that can convert DICOM files to a file format that is compatible with 2D, 3D, and/or 4D printers. What is meant by 4D printing is the printing of structures that can transform in a pre-programmed way in response to a stimulus. In another example, converting cloud may be associated with a file converting service that can convert DICOM files to a file format that is compatible with holographic displays. In one embodiment, converting cloud can include one or more conversion servers 114 to provide file conversion services, one or more databases to store images and other medical data and/or store any file format that is compatible with 2D, 3D, and/or 4D printer or holographic displays, and one or more routers to transfer data to/from other entities (not shown). If the cloud server consists of a server cluster, or more than one server, rules may exist which control the transfer of data between the servers in the cluster.

Conversion server 114 may be a file conversion server to provide services related to converting DICOM files/non-DICOM files to a file format that is compatible (or readable) with 2D, 3D, and/or 4D printers over a network. Conversion server 114 may be a file conversion server to provide services related to converting DICOM files to a file format that is compatible (readable) with holographic displays over a network. Conversion server 114 can receive the DICOM file. Conversion server 114 can receive the anonymized and/or de-identified DICOM file. DICOM file is only an example of the type of file but the file can be any imaging file. The conversion can convert, for example, the DICOM file to, for example, OBJ, STL, VRML, X3G, PLY, FBX, HDF, any other compatible format, or any combination thereof.

For example, one or more users can manipulate an image on the client application (e.g., image processing software) on the client device 113 and print the image from the client application. Server 109 can receive the print request from the client application and can create a DICOM file with information related to how the image is displayed at that time on the client application (i.e., what is seen on the display can be the same as the 3D printed model). Server 109 can transmit the created DICOM file to conversion server 114 to perform the file conversion. The format for the file conversion can be compatible with 2D, 3D, and/or 4D printers. The format for the file conversion can be compatible with holographic displays.

Database in the conversion cloud can be similar to database 110. Database can store DICOM, non-DICOM, OBJ, STL, VRML, X3G, PLY, FBX, HDF, any other compatible printing format, or any combination thereof.

According to one embodiment, converting server 114 is configured to provide file converting services to clients 113, which may represent physicians from medical institutes, agents from insurance companies, patients, medical researchers, technicians, specialist, or any combination thereof. Converting server 114 can anonymize and/or de-identify any data files to remove any Protected Health Information.

In one embodiment, printing cloud may represent a set of servers or clusters of servers associated with one or more service provider and geographically distributed over a network. For example, printing cloud may be associated with a printing service that can receive and print a file compatible with printing (e.g., 2D, 3D, 4D, holographic). In one embodiment, printing cloud can include one or more printing servers 115 to provide printing services, one or more databases to store images and other medical data and/or store any file format that is compatible with 2D, 3D, and/or 4D printing or holographic displays, and one or more routers to transfer data to/from other entities (not shown). If the printing server consists of a server cluster, or more than one server, rules may exist which control the transfer of data between the servers in the cluster.

Printing server 115 may be a printing server to provide services related to 2D, 3D, 4D, or holographic printing over a network. Printing server 115 can receive the compatible printing file. For example, printing server 115 can receive the compatible printing file from conversion server 114 to print the file. Printing server 115 can remove PHI, anonymize data, and/or de-identify data. Database in the printing cloud can be similar to database 110. Database can store DICOM, non-DICOM, OBJ, STL, VRML, X3G, PLY, FBX, HDF, AMF, STP, any other compatible printing format, or any combination thereof.

FIG. 1 show one exemplary embodiment, however, any of the servers, databases, clouds, and/or institutes can be integrated together (not shown). For example, cloud 103 and converting cloud can be combined such that only one database or one server is required.

Thus, using a cloud-based system for advanced image processing and printing has several advantages. A cloud system refers to a system which is server-based, and in which the software clients are very thin-possibly just a web browser, a web browser with a plug-in, or a mobile or phone application, etc. The server or server cluster in the cloud system is very powerful computationally and can support several users simultaneously. The server may reside anywhere and can be managed by a third party so that the users of the software in the cloud system do not need to concern themselves with software and hardware installation and maintenance.

Cloud computing provides computation, software, data access, storage services, and printing services that do not require end-user knowledge of the physical location and configuration of the system that delivers the services. Cloud computing providers deliver applications via the Internet, which are accessed from Web browsers, desktop and mobile apps, while the business software and data are stored on servers at a remote location. Cloud application services deliver software as a service over the Internet, eliminating the need to install and run the application on the customer's own computers and simplifying maintenance and support.

A cloud system can be implemented in a variety of configurations. For example, a cloud system can be a public cloud system, a community cloud system, a hybrid cloud system, a private cloud system, or a combination thereof. Public cloud describes cloud computing in the traditional mainstream sense, whereby resources are dynamically provisioned to the general public on a self-service basis over the Internet, via Web applications/Web services, or other internet services, from an off-site third-party provider who bills on a utility computing basis. Community cloud shares infrastructure between several organizations from a specific community with common concerns (security, compliance, jurisdiction, etc.), whether managed internally or by a third-party and hosted internally or externally. The costs are spread over fewer users than a public cloud (but more than a private cloud), so only some of the benefits of cloud computing are realized. Hybrid cloud is a composition of two or more clouds (private, community, or public) that remain unique entities but are bound together, offering the benefits of multiple deployment models. Briefly, it can also be defined as a multiple cloud systems which are connected in a way that allows programs and data to be moved easily from one deployment system to another, as shown in FIG. 1. Private cloud is infrastructure operated solely for a single organization, whether managed internally or by a third-party and hosted internally or externally. Generally, access to a private cloud is limited to that single organization or its affiliates.

With cloud computing, users of clients such as clients 113 do not have to maintain the software and hardware associated with the image processing. In some situations, there may be a small software installation, like a Citrix or java or plug-in. Such a configuration lowers up-front and maintenance costs for the users and there is no or lower hardware, software, or maintenance costs. The cloud servers can handle backups and redundancies and security so the users do not have to worry about these issues. The users can have access to all and the newest clinical software without having to install the same. Tools and software are upgraded (automatically or otherwise) at the servers to the latest versions. Access to tools such as printing can be driven by access level, rather than by software limitations. Cloud servers can have greater computational power to preprocess and process images and they can be larger and more powerful with better backup, redundancy, security options.

According to one embodiment, printing services provided by cloud can be provided based on a variety of licensing models, such as, for example, based on the number of users, case uploads (e.g., number of cases, number of images or volume of image data), case downloads (e.g., number of cases, number of images or volume of image data), number of cases processed and/or viewed, image processing requirements, type of user (e.g., expert, specialty or general user), by clinical trial or by research study, type of case, bandwidth requirements, processing power/speed requirements, priority to processing power/speed (e.g., system in ER may pay for higher priority), reimbursement or billing code (e.g., user may only pay to perform certain procedures that are reimbursed by insurance), time using software (e.g., years, months, weeks, days, hours, even minutes), time of day using software, number of concurrent users, number of sessions, print size, number of prints, print volume (per cmA3), file size, amount of image manipulation, types material for printing, color of printing, or any combination thereof.

In another embodiment, sever 109, conversion server 114, and/or printing server 115 can have an anonymization module which can take the DICOM file and remove PHI. In another embodiment, cloud 103, converting cloud, and/or printing cloud can have a separate server for anonymization. In another embodiment, there can be a separate server that can de-identify and/or anonymize the DICOM file before it is uploaded to cloud 103, converting cloud, and/or printing cloud.

In one embodiment, a user can specify items to be anonymized, where each item is specified in one of the entries listed in GUI 1100, as shown in FIG. 7. Each item is referenced by its DICOM tag 1101, name 1102, original value 1103 to be replaced, and replacement value 1104 to replace the corresponding original value. In this example, as shown in FIG. 7, a user can set the new value by clicking column 1104 and enter the new value. If the DICOM tag is a data type, a data selector will be displayed to allow the user to select the data. If the values allowed are predefined, a drop-down list is displayed for selecting one of the predefined values or strings. If there is a mask defined for the tag, a masked edit GUI is displayed to allow the user to change the value according to the displayed mask. The user input maybe examined by the system based on the type of the DICOM tag. If the information is incorrect, the user may be prompted to reenter the correct value. After all user inputs are collected, a new anonymous template or configuration file is created and stored. Also note that the formats or configurations of the GUIs in FIG. 7 are described for the purpose of illustration only; other formats or layouts may also be utilized. The GUI may be in the form of a browser or a phone or other mobile device application.

Gateway managers 107 and/or servers can anonymize the data. The 3D medical image data is anonymized including removing certain metadata associated with the 3D medical image data based on an anonymization template. The anonymized 3D medical image data is then automatically uploaded to a cloud server over a network.

While FIG. 1 shows a 3D printing cloud based workflow, the workflow can be locally sited in order to deploy all the components of the workflow within a specific environment such as a hospital and a hospital network that is run within a specific LAN/MAN without any cloud access.

Figure 2:
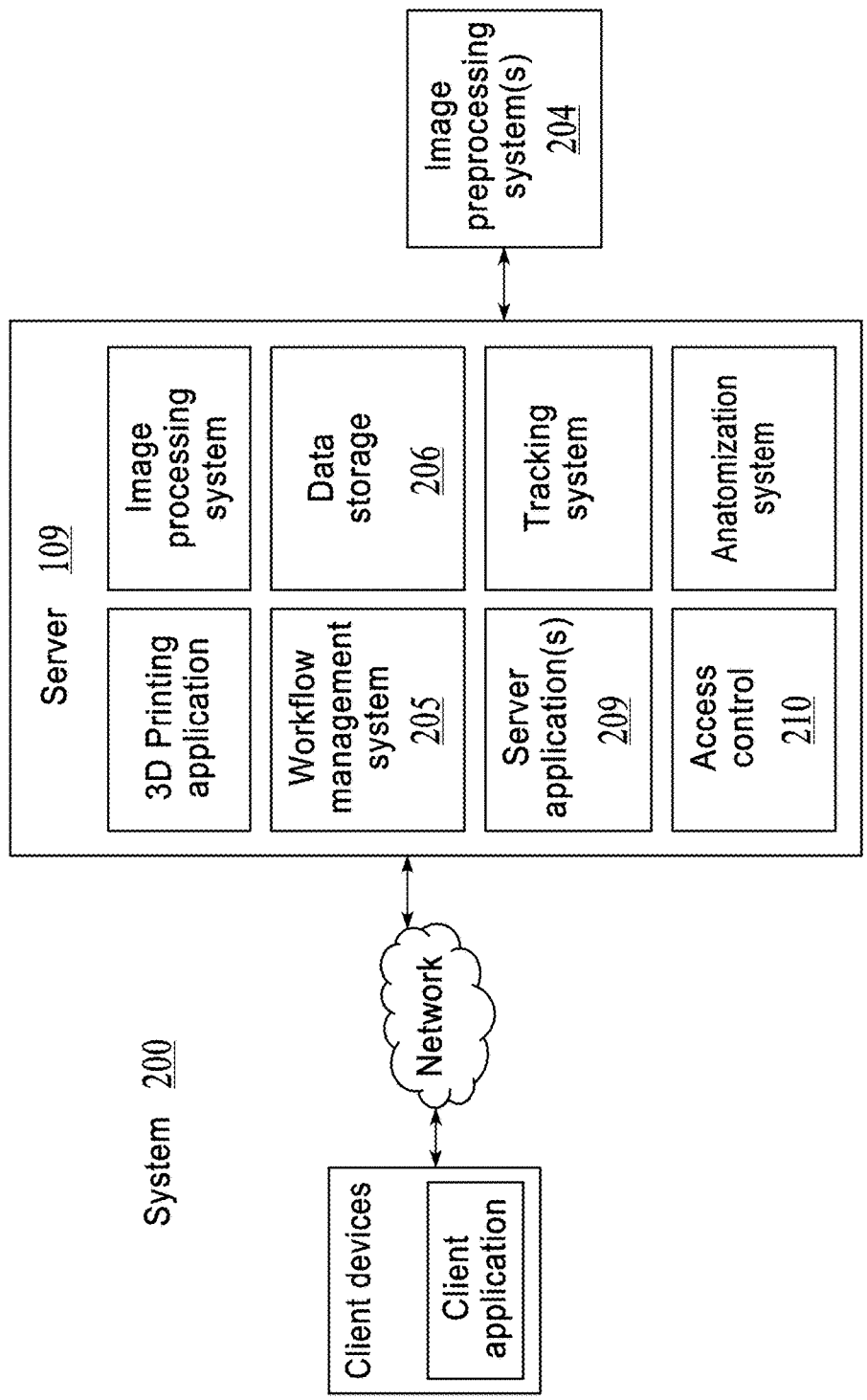
FIG. 2 is a simplified block diagram illustrating data access control and image processing for 3D printing.

FIG. 2 is a block diagram illustrating a cloud-based image processing system with 3D printing (referred to as 3D Printing System) according to one embodiment. The 3D Printing System can an imaging processing server communicatively coupled to one or more clients over a network, which may be a LAN, MAN, WAN, or any combination thereof. The image processing server is configured to provide cloud-based image processing services with 3D printing to clients based on a variety of printing licensing models. Each client can include a client application to communicate with an image processing server application in the image processing server to access resources provided by image processing server. Image processing system can be implemented as a virtual server or instance of the image processing application, one for each client.

According to one embodiment, server 109 includes, but is not limited to, workflow management system 205, medical data storage 206, image processing system 207, access control system 210, 3D printing application, tracking system, or any combination thereof. Medical data store 206 may be implemented as part of database 110 of FIG. 1. Medical data store 206 is utilized to store medical images, image data received from medical data center (e.g., PACS systems) 105 or other image storage systems 215 (e.g., CD-ROMs, or hard drives) and processed by image processing system 207 and/or image preprocessing systems 204, DICOM, OBJ, STL, VRML, X3G, PLY, FBX, HDF, AMF, STP, any other compatible printing format, holographic display formats, or any combination thereof. Image processing system 207 includes a variety of medical imaging processing tools or applications that can be invoked and utilized by clients via their respective client applications, respectively, according to a variety of licensing terms or agreements.

In response to image data received from medical data center or from image capturing devices (not shown) or from another image source, such as a CD or computer desktop, according to one embodiment, image preprocessing system 204 may be configured to automatically perform certain preprocesses of the image data and store the preprocessed image data in medical data storage 206. For example, upon receipt of image data from PACS 105 or directly from medical image capturing devices, image preprocessing system 204 may automatically perform certain operations, such as bone removal, centerline extraction, sphere finding, registration, parametric map calculation, reformatting, time-density analysis, segmentation of structures, and auto-3D operations, and other operations. Image preprocessing system 204 may be implemented as a separate server or alternatively, it may be integrated with server 109. Furthermore, image preprocessing system 204 may perform image data preprocesses for multiple cloud servers such as server 109.

In one embodiment, a client/server image data processing architecture can be installed on system 200. The architecture can include client partition (e.g., client applications) and server partition (e.g., server applications 209). The server partition of system 200 can run on the server 109, and communicates with its client partition installed on clients, respectively. In one embodiment, server 109 is distributed and running on multiple servers. In another embodiment, the system is a Web-enabled application operating on one or more servers. Any computer or device with Web-browsing application installed may access and utilize the resources of the system without any, or with minimal, additional hardware and/or software requirements.

In one embodiment, server 109 may operate as a data server for medical image data received from medical image capturing devices. The received medical image data is then stored into medical data store 206. In one embodiment, for example, when client 202 requests for unprocessed medical image data, server application 209 retrieves the data from the medical data store 206 and renders the retrieved data on behalf of client 202.

Image preprocessing system 204 may further generate workflow information to be used by workflow management system 205. Workflow management system 205 may be a separate server or integrated with server 109. Workflow management system 205 performs multiple functions according to some embodiments of the invention. For example, workflow management system 205 performs a data server function in acquiring and storing medical image data received from the medical image capturing devices. It may also act as a graphic engine or invoke image processing system 207 in processing the medical image data to generate 2D or 3D medical image views.

In one embodiment, workflow management system 205 invokes image processing system 207 having a graphics engine to perform 2D and 3D image generating. When a client (e.g., clients) requests for certain medical image views, workflow management system 205 retrieves medical image data stored in medical data store 206, and renders 2D or 3D medical image views from the medical image data. The end results for medical image views are sent to the client.

In one embodiment, when a user making adjustments to the medical image views received from server 109, these user adjustment requests are sent back to the workflow management system 205. Workflow management system 205 then performs additional graphic processing based on the user requests, and the newly generated, updated medical image views are returned to the client. This approach is advantageous because it eliminates the need to transport large quantity of unprocessed medical image data across network, while providing 2D or 3D image viewing to client computers with minimal or no 2D or 3D image processing capacity.

As described above, when implemented as a cloud based application, system 200 includes a client-side partition and a server-side partition. Functionalities of system 200 are distributed to the client-side or server-side partitions. When a substantial number of functionalities are distributed to the client-side partition, system 200 may be referred to as a "thick client" application. Alternatively, when a limited number of functionalities are distributed to the client-side partition, while the majority of functionalities are performed by the server-side partition, system 200 may be referred to as a "thin client" application. In another embodiment, functionalities of system 200 may be redundantly distributed both in client-side and server-side partitions. Functionalities may include processing and data. Server 109 may be implemented as a web server. The web server may be a third-party web server (e.g., Apache™ HTTP Server, Microsoft® Internet Information Server and/or Services, etc.).

The image processing operations receive medical image data collected by the medical imaging devices as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Various automatic and manual masking and/or coloring of the medical image views can also be captured as metadata. Thus, metadata allows the returning of the system to the state it was in when the metadata was saved. Metadata can also be used to print (e.g., 3D print) the image as displayed on the client device. Metadata can also be used to display a hologram of the image as displayed on the client device. Workflow management system 205 also allows the updating and saving of scenes during user adjustments of the medical image views generated from the scenes.

Referring back to FIG. 2, according to one embodiment, server 109 can include access control system 210 to control access of resources (e.g., image processing tools) and/or medical data stored in medical data store 206 from clients. Clients may or may not access certain portions of resources and/or medicate data stored in medical data store 206 dependent upon their respective access privileges. For example, depending on the user privileges, some users can print while other uses may not be able to print. There can be a credit system where each user preference is associated with credits. The credits can determine how much volume (cm$^\wedge$3) one can print or how many objects one can print. The tracking system can track the number of credits, prints, total volume, types of prints, or any combination thereof associated with a user.

The DICOM (Digital Imaging and Communications in Medicine) format is commonly used for the transfer and storage of medical images, such as ultrasounds and scans. DICOM files can contain both image data and headers, which can store information about the patient and the medical image. A user can open, edit, and save DICOM files. Metadata can include patient data (e.g., patient name, ID, sex, date of birth, or any combination thereof), study data (e.g., study ID, referring physician, study date and time, study description, or any combination thereof), series data (e.g., series number, modality, series date and time, series description, or any combination thereof), equipment data (e.g., the equipment institution and manufacturer), image data (e.g., the transfer syntax, photometric interpretation such as YBR full 422 and RGB, image width and height, bits per pixel, and frames), color (e.g., a surface mode that can have direction, color, rendering, and shading with shading done with color representations), texture, shape, vector information, pixel information, segmentation volumes and sub-volumes, lighting, shadowing, look-up table (LUT), multi-volume management, or any combination thereof. Such information can be included within the headers of the DICOM header files. For example, the color information can demonstrate the color surface within the headers of the DICOM header files.

Server 109 can include a 3D printing application. When the user is in a workflow, the user can manipulate the images (as described above). The manipulation of such image(s) can be saved in the metadata of the image. When the user clicks print after the user has performed manipulations of the image, the 3D application can create a new DICOM file or update the DICOM file such that the manipulations of the image are captured in the metadata. For example, the DICOM metadata can include color (e.g., a surface mode that can have direction, color, and shading with shading done with color representations), vector information, pixel information, segmentation volumes and sub-volumes, lighting, shadows, LUT, or any combination thereof. The new DICOM file or updated DICOM file can allow the user to obtain or receive a 3D print of exactly the image that is displayed on the client. There can be volumes and/or sub-volumes that can have its own LUT. The DICOM file can be created at the time the user performs the print function. In another embodiment, the DICOM file can be created/updated each time the user manipulated the image.

Referring back to FIG. 2, according to one embodiment, server 109 can include anonymization system to anonymize and/or de-identify the data to remove protected health information from the image data file, DICOM file, DICOM headers, or any other file containing protected health information. The anonymization system can anonymize and/or de-identify the data before the data is processed by server 109. The anonymization system can anonymize and/or de-identify the data before the data is sent to converting cloud.

Figure 3:
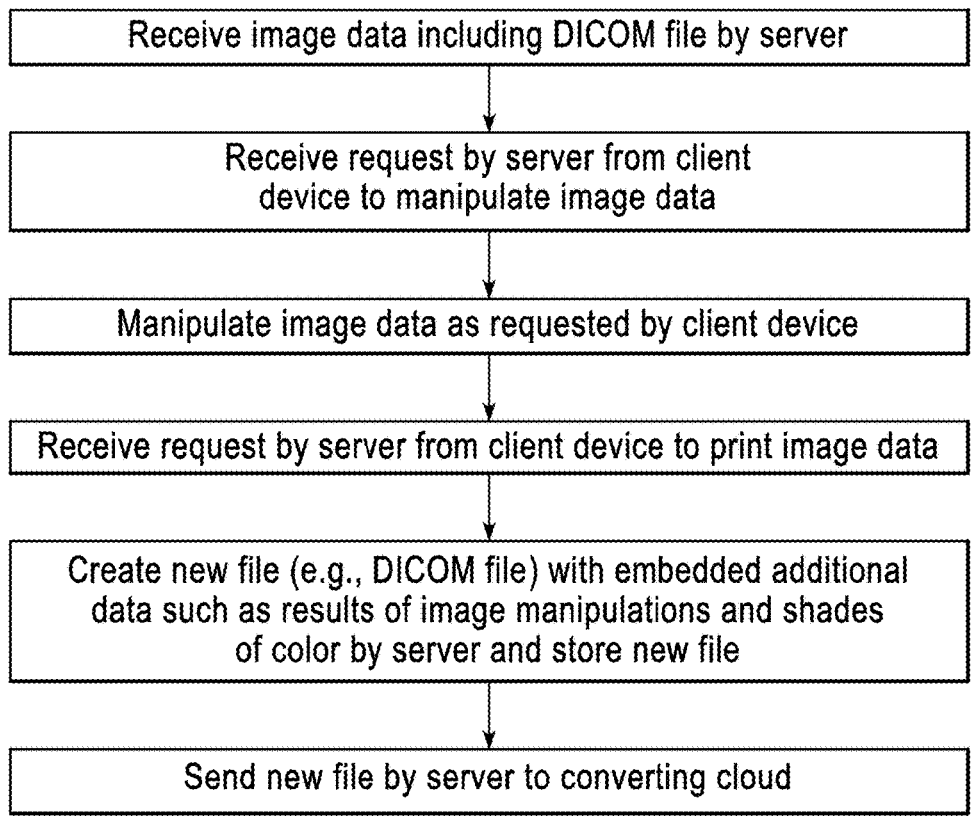
FIG. 3 and FIG. 4 are simplified flowcharts illustrating a workflow for a printing process.

FIG. 3 is a flow diagram illustrating a method for the cloud-based image processing system with 3D Printing according to one embodiment. Method may be performed by a server such as server 109. Image data (including, for example, DICOM Files) can be received at a server from a storage medium (e.g., PACS, cloud based storage, local drive, CD, hard drive, DVD, USB, web uploader, any DICOM folder on a client device, or any combination thereof) over a network. The server can receive requests from client device to manipulate (i.e., segment, color, mask, manually process, automatically process, preprocess, or any combination thereof) image data. The server can manipulate image data as requested by the client device. The server can receive a request by the client device to print the image data. The server can create new file (e.g., DICOM file) with embedded additional data such as results of image manipulations and shades of color by server. For example, the new DICOM file can include color (e.g., a surface mode that can have direction, color, and shading with shading done with color representations), vector information, pixel information, segmentation volumes and sub-volumes, lighting, shadows, LUT values, brightness, opacity, or any combination thereof. The server can store the new DICOM file in the database. The server can send the new DICOM file to the converting cloud.

Figure 4:
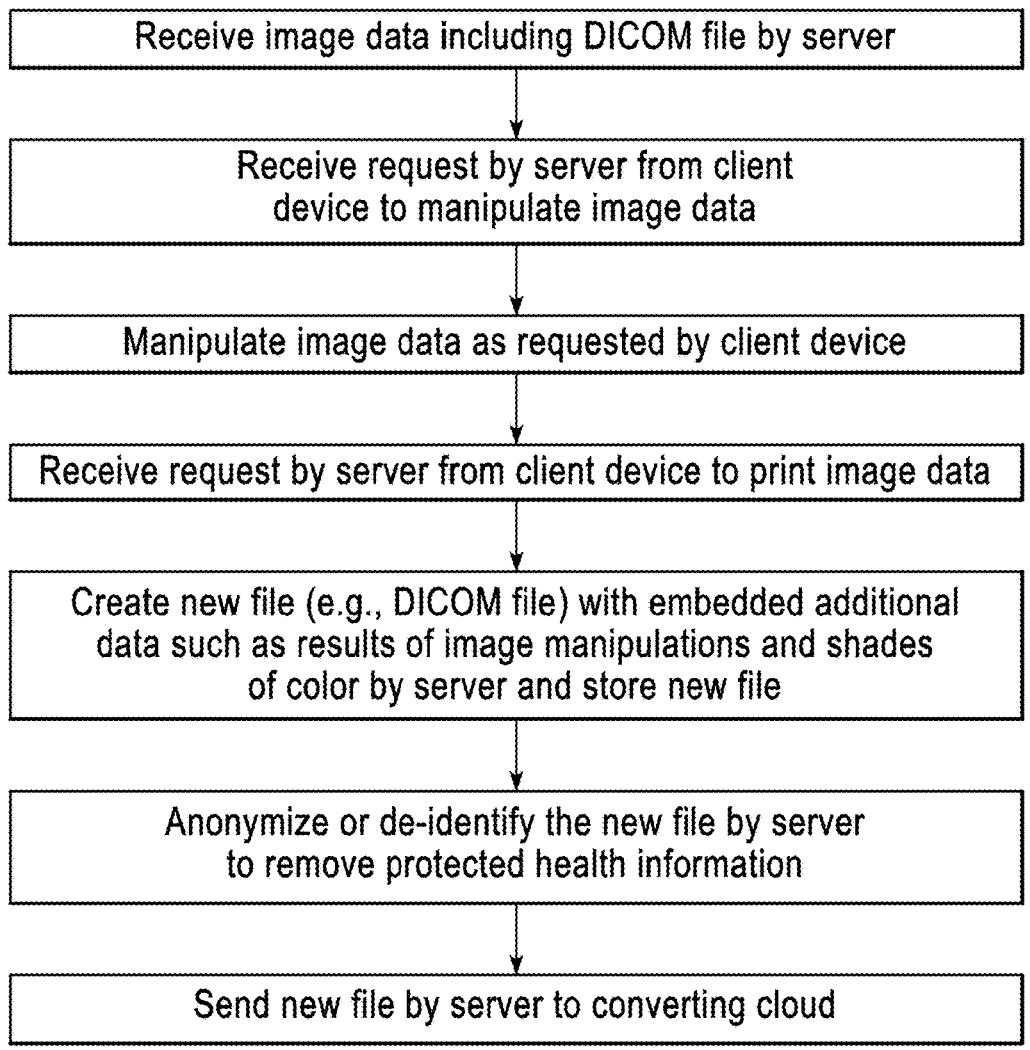

FIG. 4 is a flow diagram illustrating a method for the cloud-based image processing system with 3D Printing according to one embodiment. Method may be performed by a server such as server 109. Image data (including DICOM Files) can be received at a server from a storage medium (described above) over a network. The server can receive requests from client device to manipulate (described above) image data. The server can manipulate image data as requested by the client device. The server can receive a request by the client device to print the image data. The server can create new file (e.g., DICOM file) with embedded additional data such as results of image manipulations and shades of color by server. The server can store the new DICOM file in the database. The server can anonymize or de-identify the new file to remove protected health information (e.g., patient name, date of birth, etc.). The server can send the new file to the converting cloud. In another embodiment, the image data file can be anonymized or de-identified before being received by the server 109.

Figure 5A:
FIG. 5A, FIG. 5B, FIG. 5C, FIG. 5D, FIG. 5E and FIG. 5F illustrate use of a graphics user interface to generate a segmented model which can be sent to a 3D printing cloud.
Figure 5B:
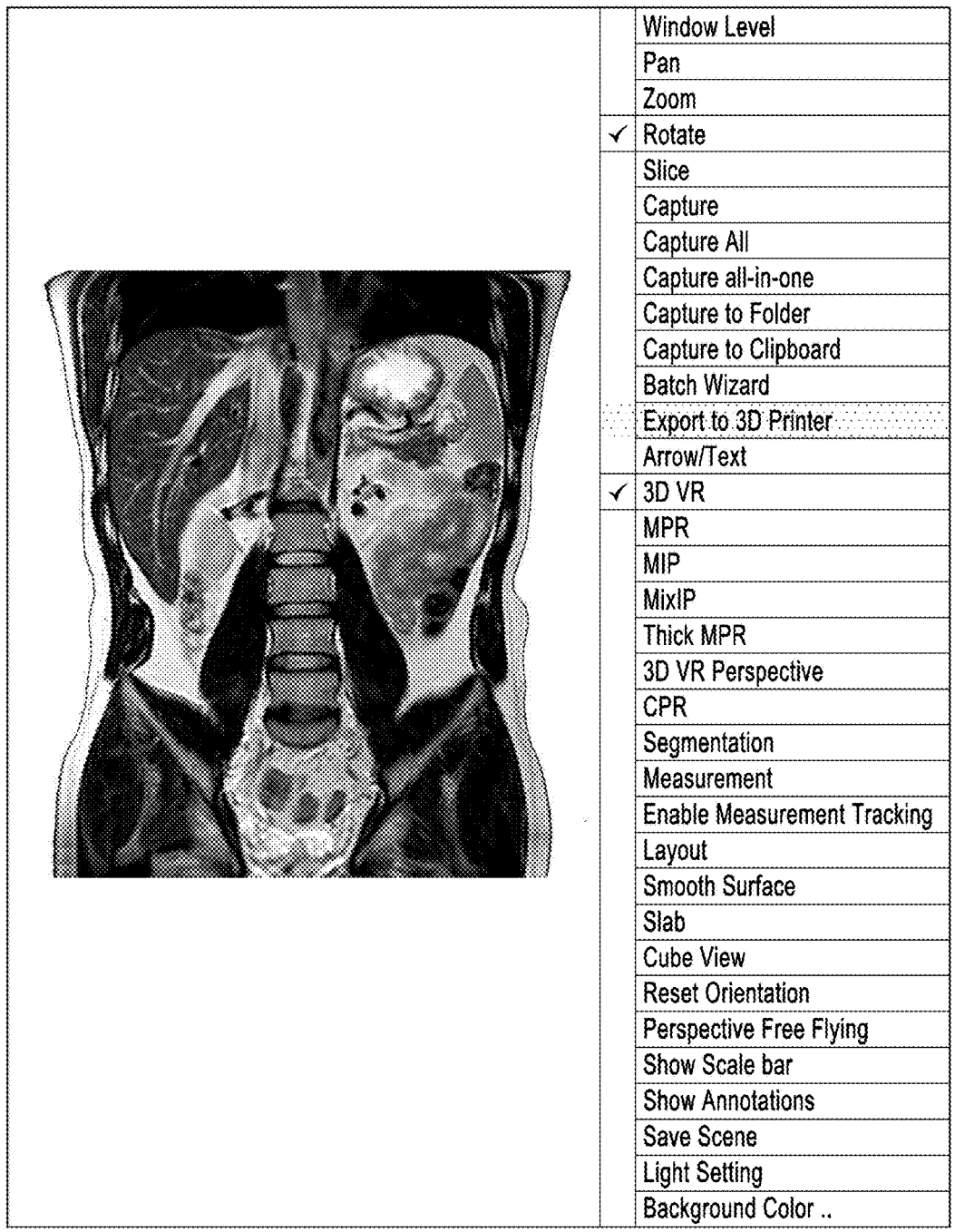
Figure 5C:
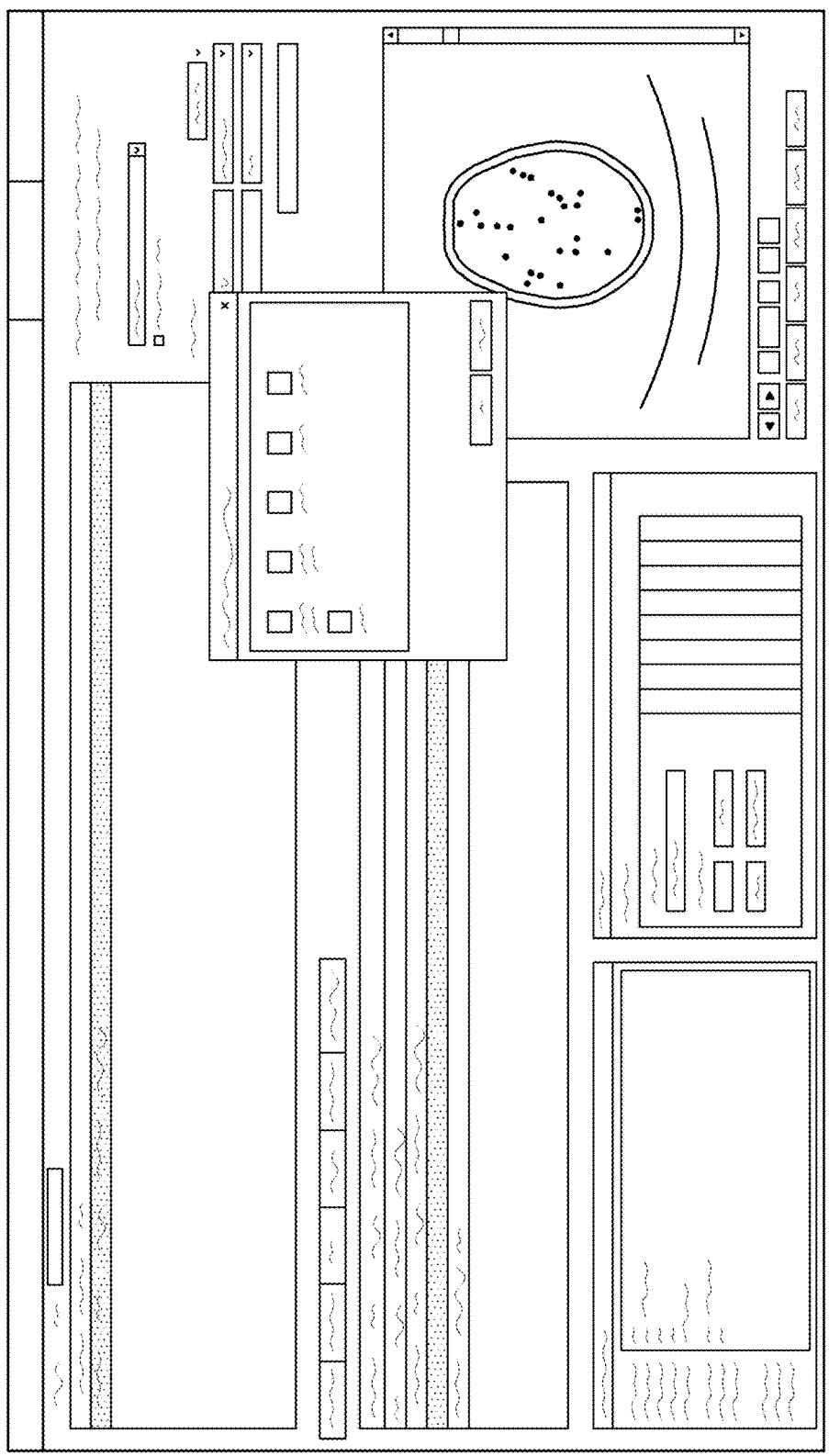
Figure 5D:
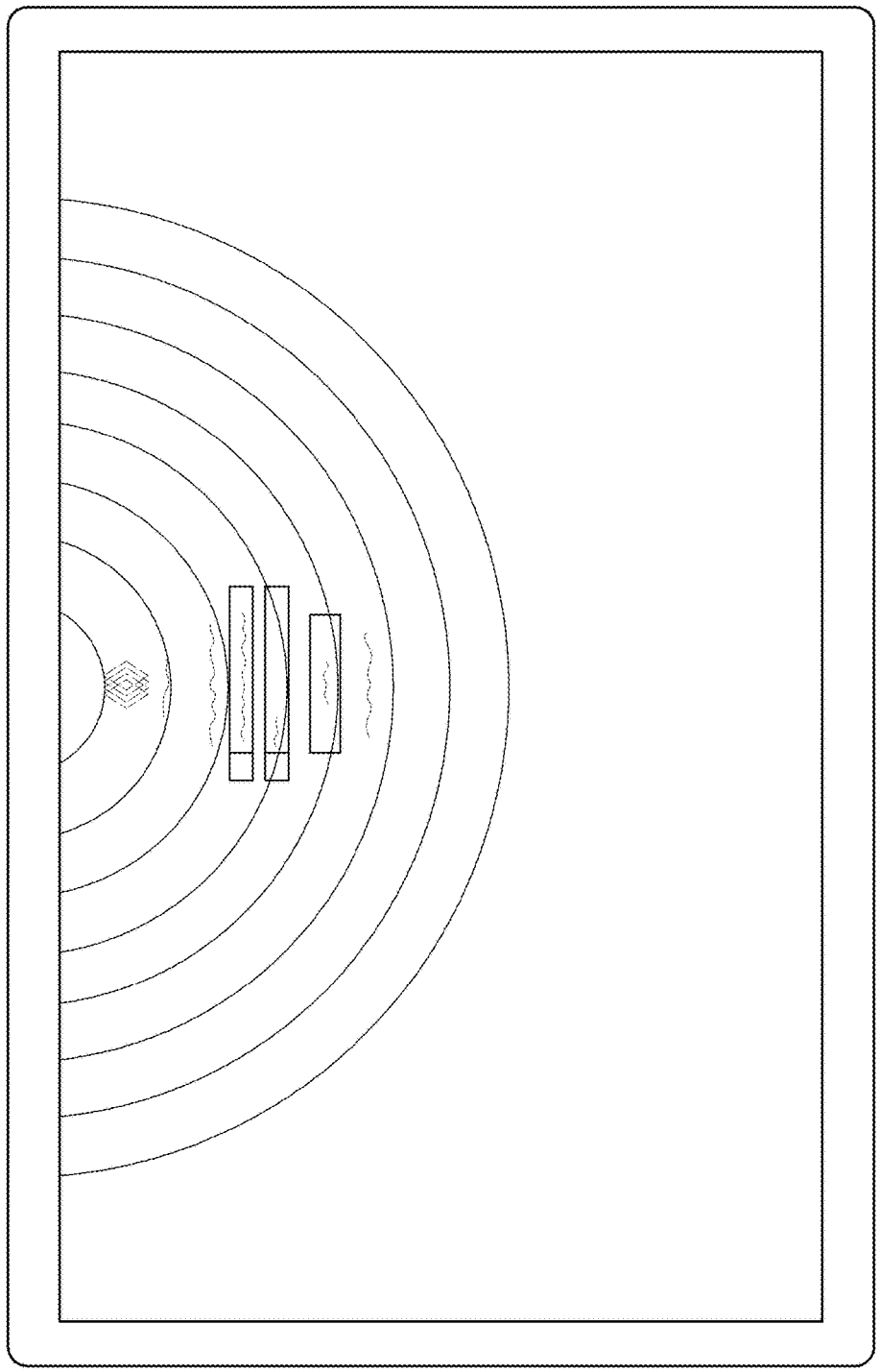
Figure 5E:
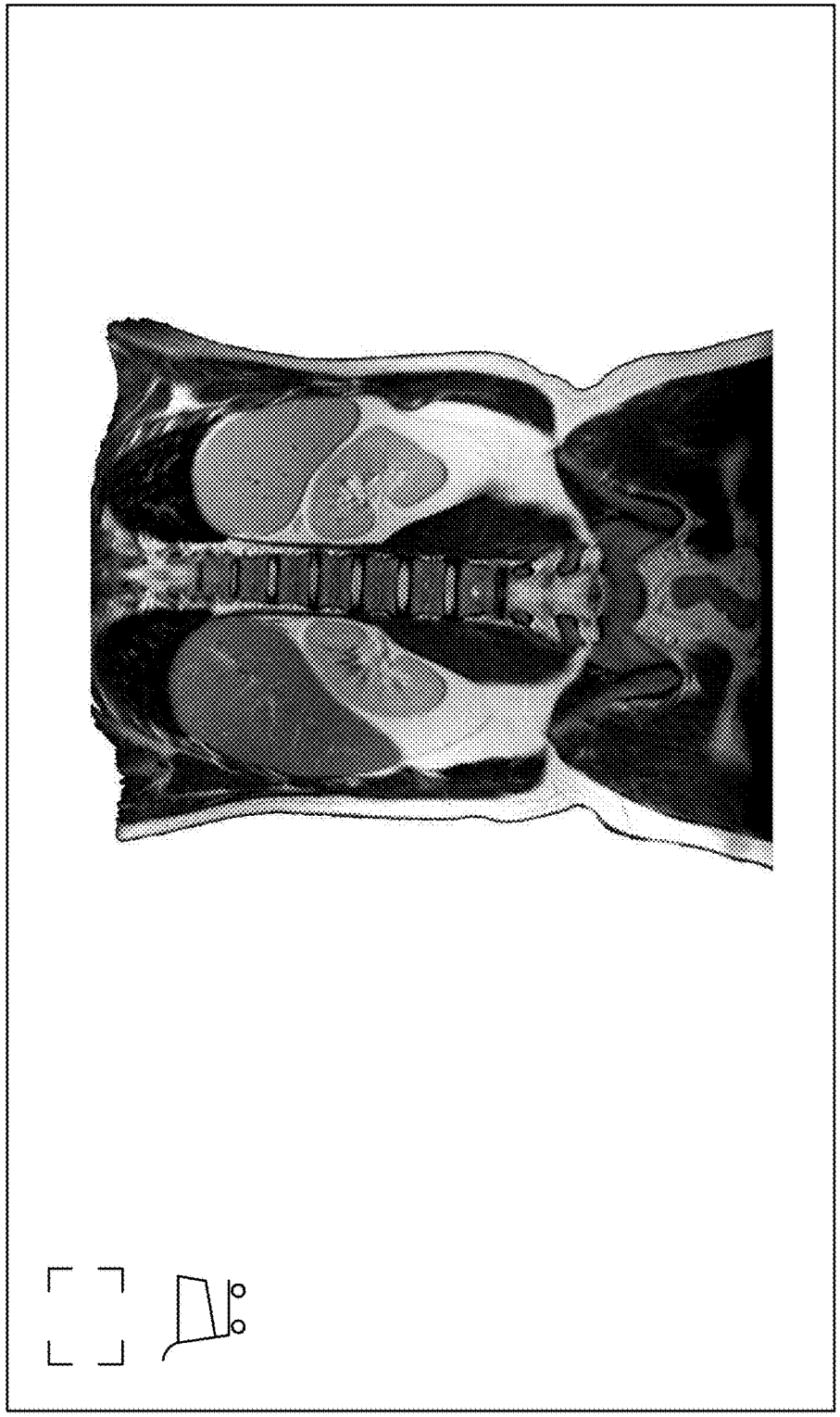
Figure 5F:
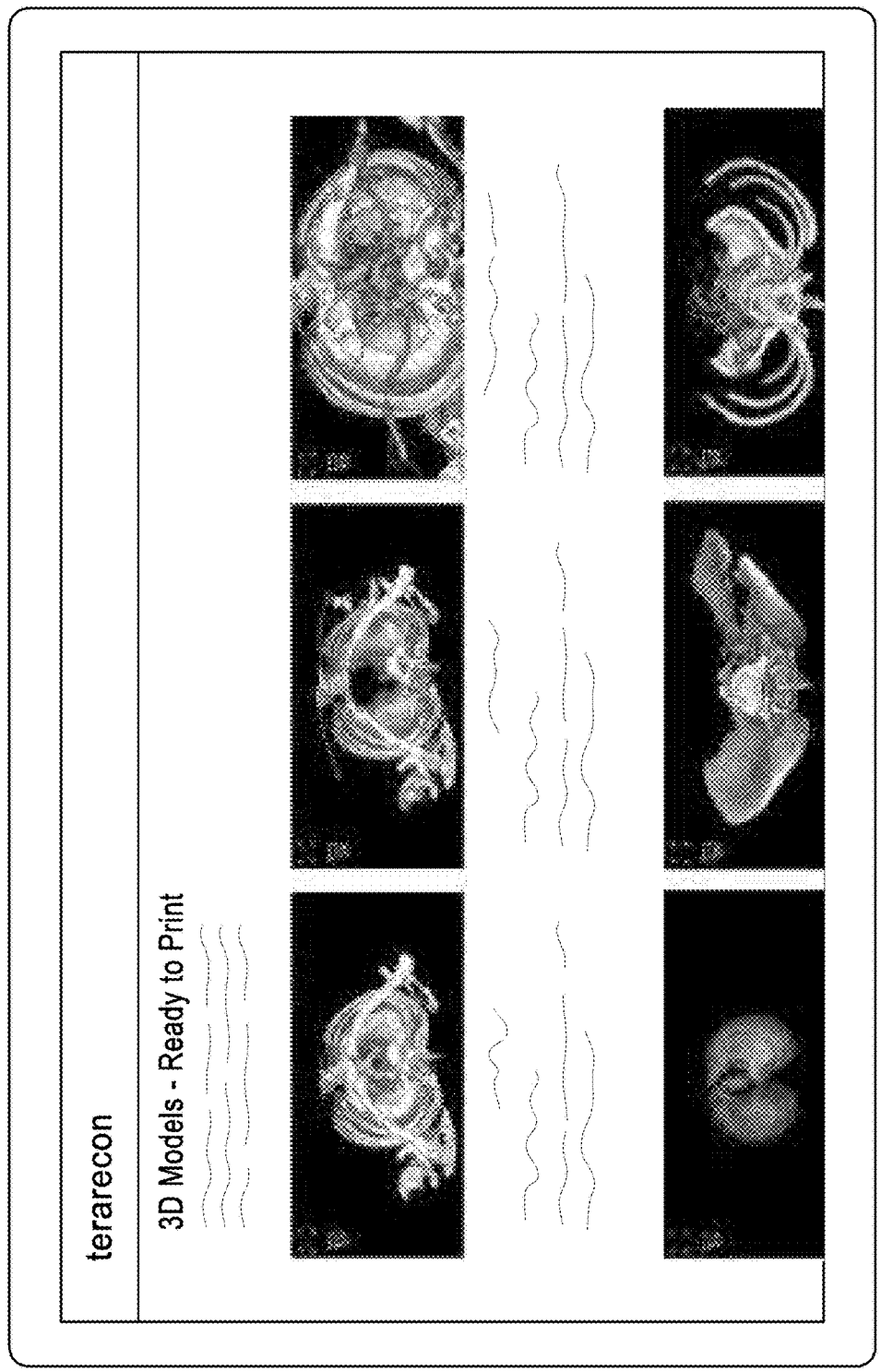

In one embodiment, the new file format based on the DICOM format can avoid STL conversion. In one embodiment, the new format can allow to export the model to be printed "as is" and keep the high-quality image resolution. In one embodiment, server 109 can track the progress of the upload of the model. In one embodiment, the server can perform a drag and drop request by the client device to upload the image data to the client viewer. FIGS. 5A-5E are screenshots illustrating certain GUIs of cloud-based image processing system with 3D Printing according to one embodiment. GUIs of FIGS. 5A-5E may be presented by a client application (e.g., a thin client) or web-based application operated by various users. For example, FIG. 5A can represent a GUI page operated by a user that can have an anatomical image that may have been pre-processed or manipulated by the user to color, mask, highlight, or remove certain areas via tools in the client application. Referring to FIG. 5A, in this example, the user can view the anatomical image in the 3D overview view. Referring to FIG. 5B, the user can click and have a number of tools and options. For example, one option can be to export to 3D printer. Referring to FIG. 5C, the exported file to be printed can support the DICOM protocol transfer. The exported file can be pushed to a DICOM node to upload the model to a user account. The user can have an automation option to create an auto forward of the 3D models to the user's 3D printing account. FIG. 5D can represent a GUI page operated by a user that has access control to the user's printing account. The user's printing account can be hosted on the cloud or in a web environment. Each user can manage their own user library. FIG. 5E can represent a GUI page operated by a user where each model can be previewed and confirmed before the model production (i.e., 3D printing begins). The user can click the shopping cart icon when the user confirms that the model is ready for printing. FIG. 5E represents a GUI page operated by a user where each user can have access to their own model library. The models that are pushed to the user's account can be ready for printing. The 3D model received by the user can be the same model created from the image processing platform.

Figure 6:
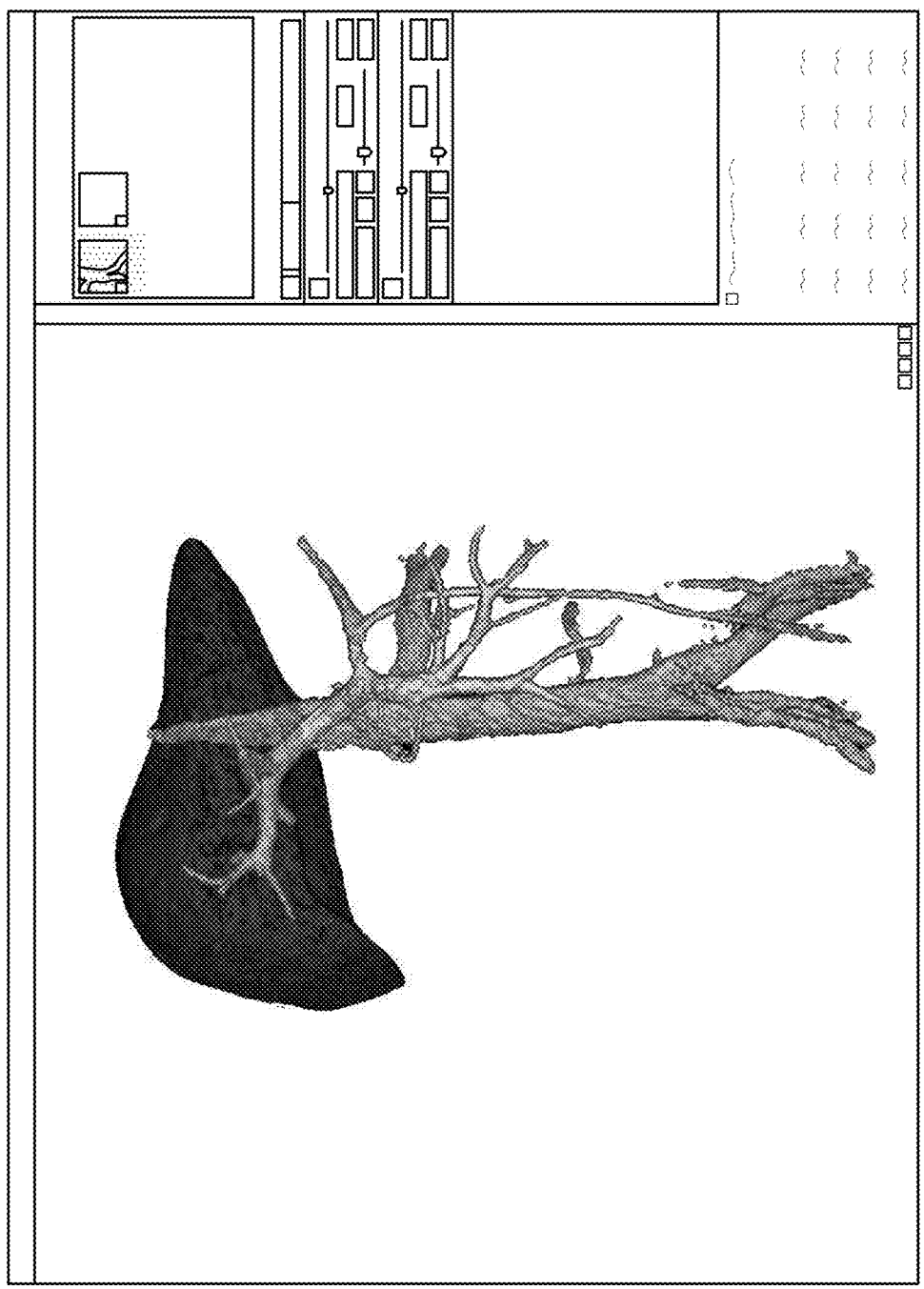

FIG. 6 is a screenshot illustrating certain GUIs. FIG. 6 can represent a GUI page operated by a user that can have an anatomical image. The user can view the LUT (one or multiple) applied to any particular sub-volume (region of interest) or all of them and utilize the options to manipulate the images. The LUT can include, but is not limited to, tools to manipulate WW, WL, opacity, brightness, ramp-up linear, right-recline triangle, ramp-up linear, color, mask, texture, or any combination thereof. The values of the LUT can be included in the new DICOM file (as described above) or updated in the DICOM file.

In one embodiment, the cloud-based image processing system with 3D Printing can export from image processing server as DICOM. In one embodiment, the cloud-based image processing system with 3D Printing can support multiple volumes. In one embodiment, the cloud-based image processing system with 3D Printing can support LUT per volume/sub-volume (i.e., each volume can have its own LUT). In one embodiment, the cloud-based image processing system with 3D Printing can embed the LUT.

Figure 8:
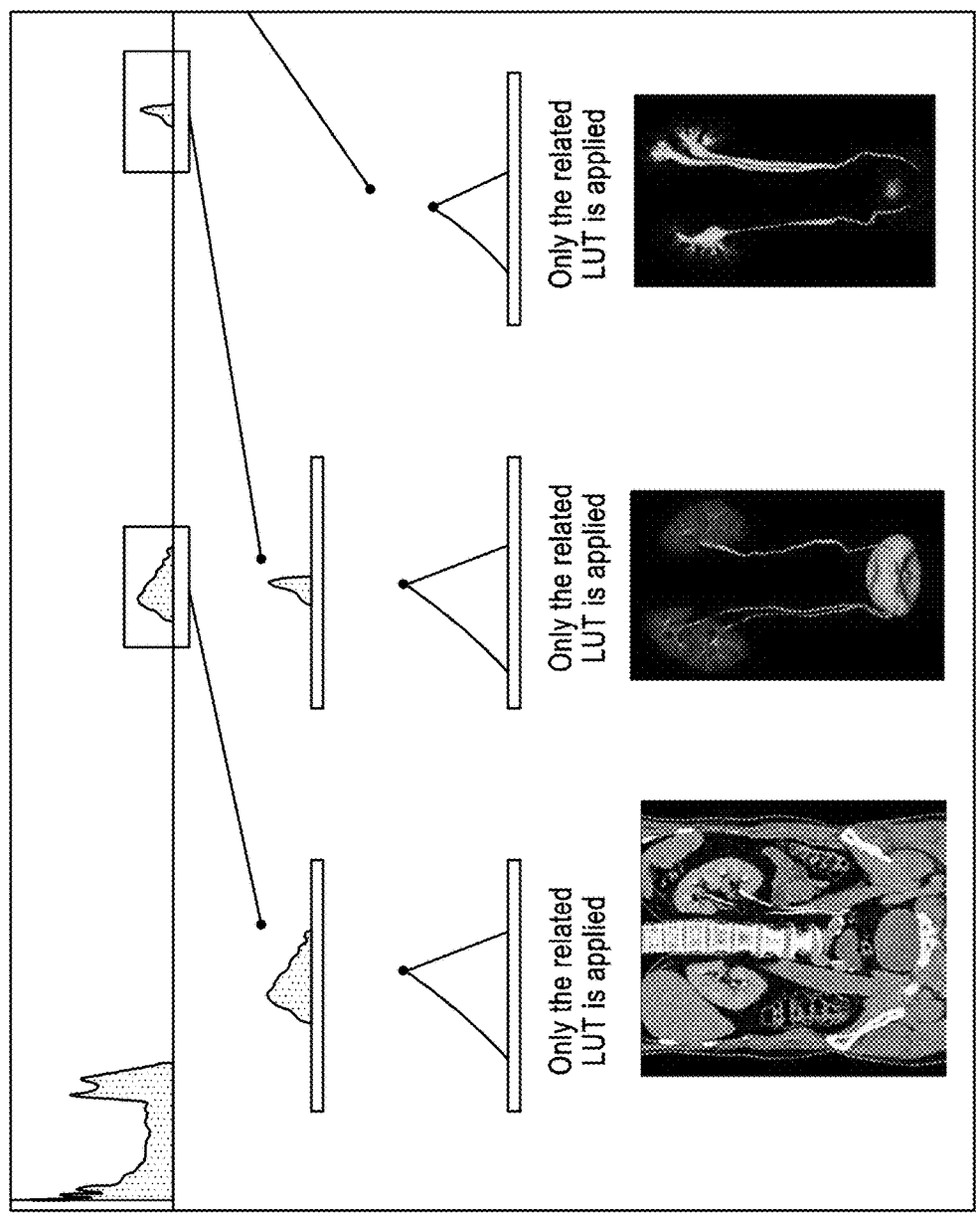

FIG. 8 illustrates a graph for LUT and masking according to one embodiment. This technic allows the medical volume to be processed with multiple sub volume to clearly identify particular human body structure such as bone, vessels, organ, tumor etc. and applied them a particular rendering (color, shadow, transparency, opacity, texture etc.). The technic also allows creation of a sub-volume optimized rendering which will be used to create a print-ready file for 3D printing. This technic also allows rendering of a hologram of a patient specific segmentation using holographic technic, device, and/or platform and/or a virtual representation of a patient using virtual reality technic, device and/or platform.

Figure 9:
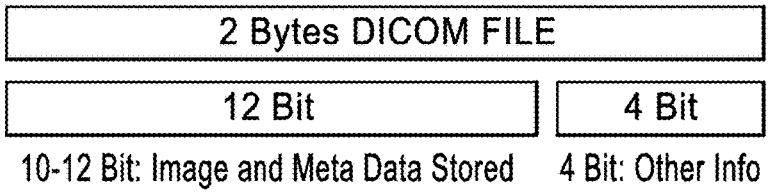
FIG. 9 is a block diagram illustrating the storage structure of a DICOM file.

FIG. 9 is a block diagram illustrating the storage structure of the DICOM file according to one embodiment. The DICOM file can be configured to store the image, metadata, and other information. Other information can include overlay objects, proprietary information (e.g., image objects, proprietary metadata, metadata not included in the original image, metadata not included in the original metadata, or any combination thereof), LUT, multi-volume management, rendering, shape, surface details, any characteristic described in this specification, or any combination thereof. The DICOM file can be about 2 bytes (i.e., about 16 Bit). The image and/or metadata can be stored in about 10 Bit to about 12 Bit of the DICOM file, for example, 10 bit, 11 bit, or 12 bit. Other information can be stored in about 1 Bit to about 4 Bit (e.g., 1 bit, 2 bit, 3 bit, or 4 bit) of the DICOM file. Other information can be stored throughout any portion of the file, for example, at the end, in the middle, in the beginning, spread within the bit storing the image and metadata information, or any combination thereof. The DICOM file (or other file types mentioned in this specification) can be converted to, for example, OBJ, STL, VRML, X3G, PLY, FBX, HDF, any other compatible format for 3D printing or holographic display, or any combination thereof.

Figure 10:
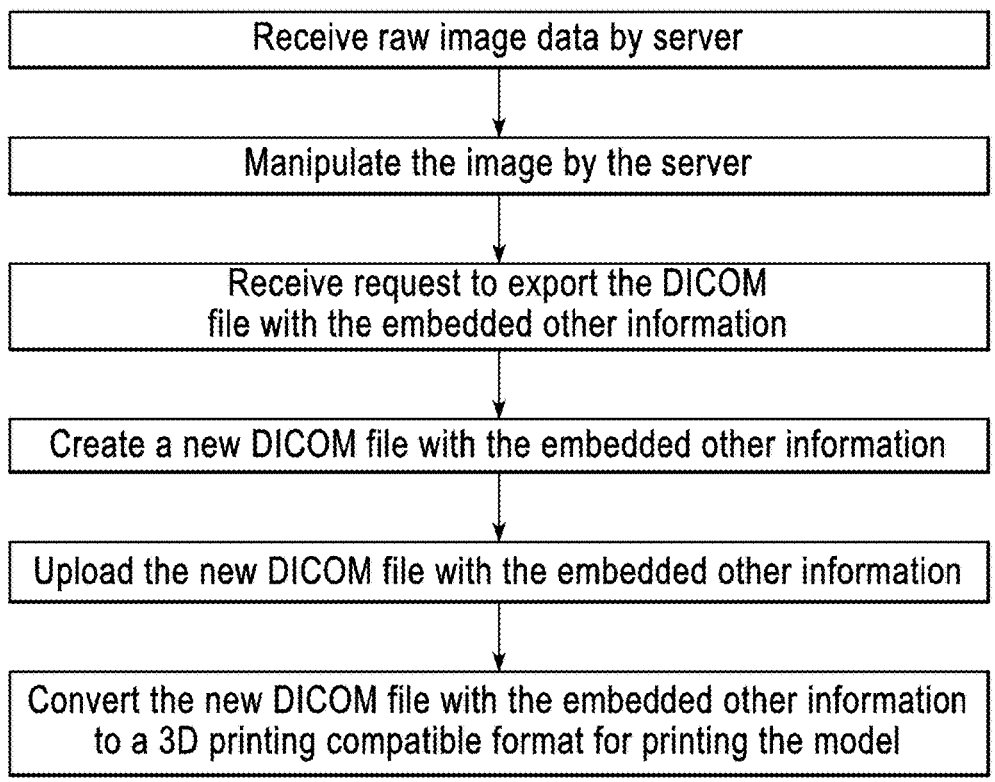
FIG. 10 and FIG. 11 illustrate a file conversion workflow performed before printing.

FIG. 10 is a flowchart illustrating the 3D Printing of a model on a Diagnostic Software Application according to one embodiment. The server can receive raw image data including, for example, the DICOM file from the medical imaging device. The server can manipulate (e.g., segment) the image data based on client applications, preprocessing servers, post-processing servers, or any combination thereof with automated, semi-automated, or manual results. The server can receive the request by the client application to export the DICOM file with the embedded other information. The embedded other information can include data related to the manipulations. The server can create a new DICOM file with the embedded other information. The server can upload the new DICOM file with the embedded other information via a DICOM push to a user account. The server can convert the new DICOM file with the embedded other information to a 3D printing compatible format (e.g., OBJ file) for printing the 3D model.

In one embodiment, the user can print the object displayed on the client such that the 3D printed model is representative of the same attributes of what is displayed on the client inclusive of any of the characteristics in the LUT and/or metadata. In other words, what the user sees on the display can be what the user receives as the 3D printed model or render in the holographic and/or virtual reality device.

Figure 11:

FIG. 11 is a block diagram illustrating the conversion of the DICOM file to another file type (e.g., OBJ) according to one embodiment. Note that the same techniques described in this specification can convert any file type (e.g., DICOM, non-DICOM, OBJ, STL, VRML, X3G, PLY, FBX, or HDF) to any file type (e.g., DICOM, non-DICOM, OBJ, STL, VRML, X3G, PLY, FBX, or HDF) for printing a 3D model from a diagnostic software application. In one embodiment, the server can convert the files automatically (i.e., no user action) or at the request of the user. The server can convert the voxel model to a polygon file format (e.g., from DICOM to OBJ). The conversion can use the new DICOM file with the embedded other Information and convert each volume with the related other information into a single printer readable format.

A segmented medical file as described above can be rendered in its raw format (DICOM) using file format description shown in FIG. 8. The render allows the user to access the 3D reconstruction as a 3-D model or a hologram regardless its viewing device. For example, the viewing device can be a virtual reality viewing device or a mixed reality (augmented reality) viewing device.

For example, the segmented model, in its raw format, is rendered on a server-side hosting or connected to one or multiple GPU. This server side rendering allows the model to be rendered regardless its file size. The rendering is the result of the volume manipulation (rotation, pan, zoom, WW/WL, cutting plan etc.). This result of manipulation is sent in real-time to the client device connected to the server using user identification. The platform allows user to connect to its own environment containing a user's specific data.

The 3D hologram and/or any loaded application can be seen in real-time by one or multiple user through a sharing function. This function allows multiple use to see the holographic environment in real-time and communicate about it. This will allow healthcare professional to communicate about the loaded image.

Figure 12:
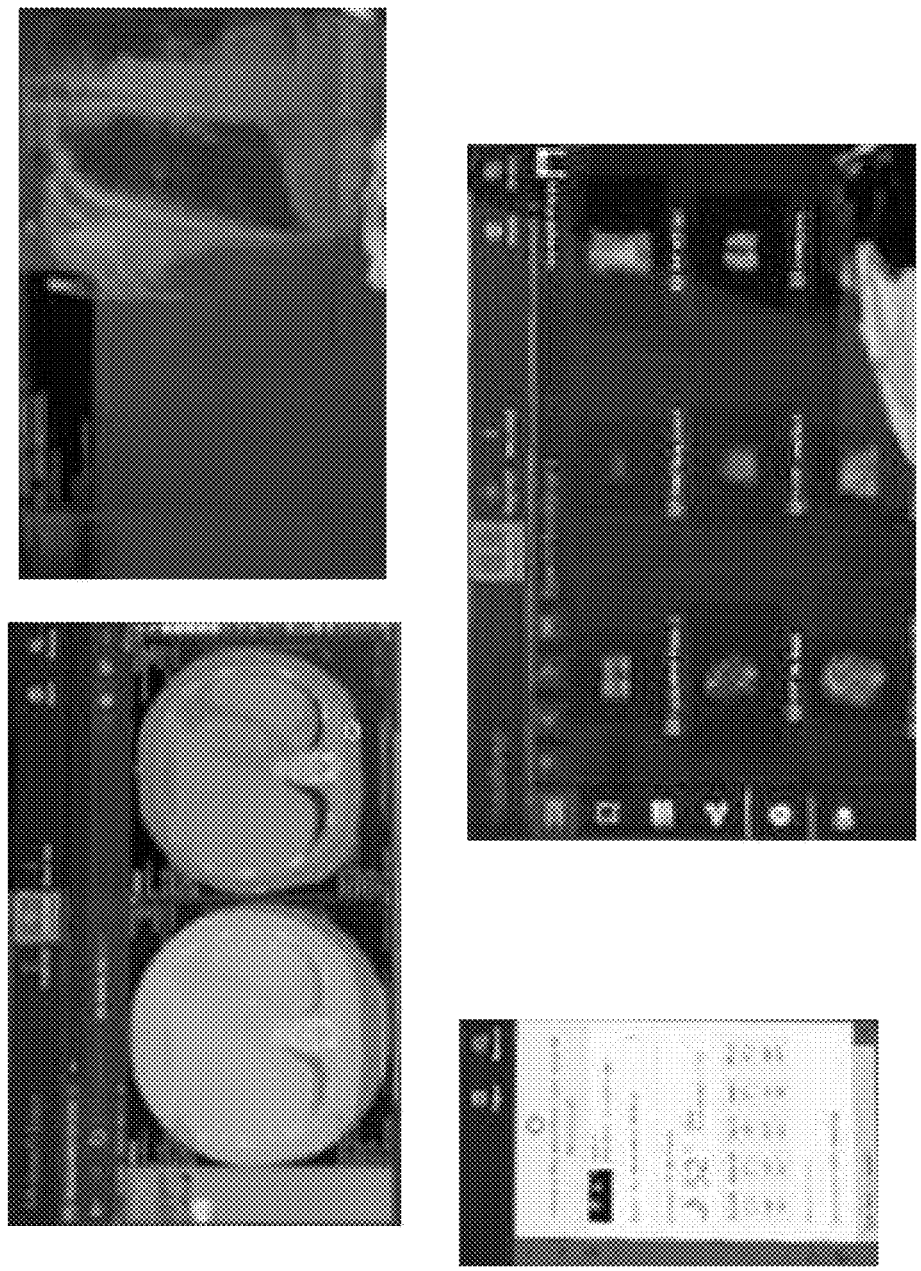
FIG. 12 illustrates a graphics user interface for a medical holographic platform that can load and render several applications.

For example, FIG. 12 illustrates a medical holographic platform which can load and render several applications where each of them has their own function, application and usage.

Figure 13:
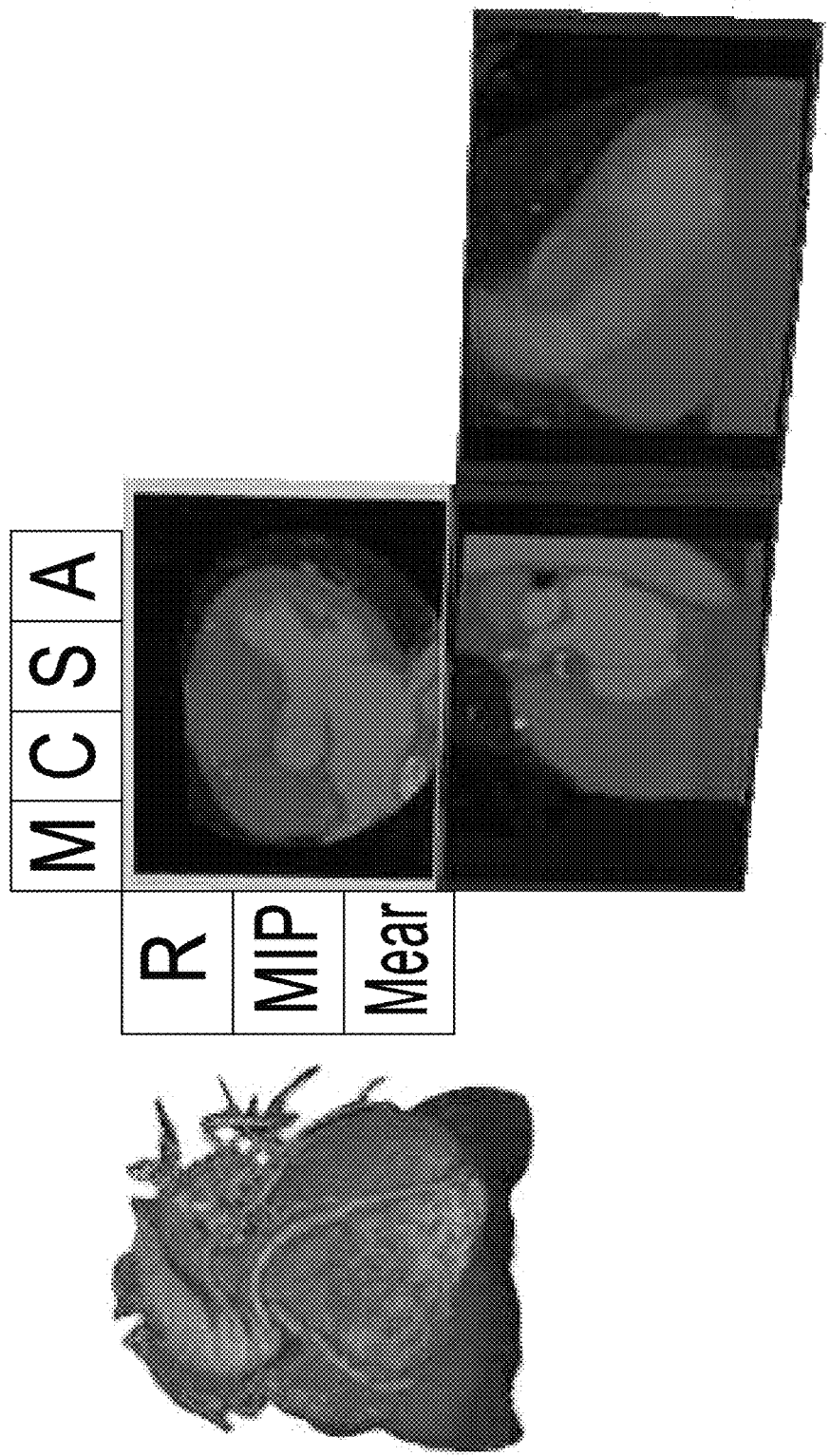
FIG. 13 illustrates a graphics user interface display of a medical volume (heart) render with an original two-dimensional (2D) radiological view (axial, coronal and sagittal).

FIG. 13 illustrates a medical volume (heart) render using pre-segmented data and customized LUT as well as it original 2D radiological view (axial, coronal and sagittal), each of the radiological views can be manipulate individually with specific rendering such as MIP and MPR.

Figure 14A:
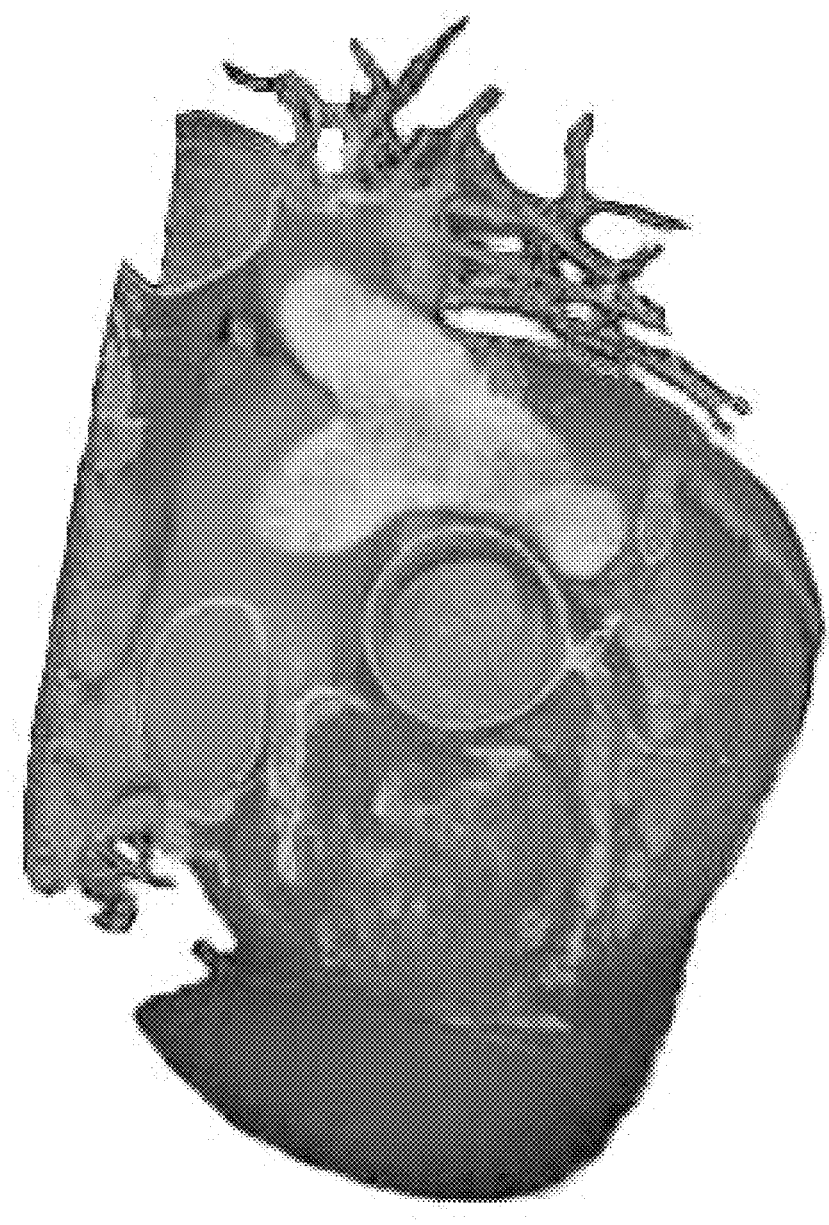
FIG. 14A and FIG. 14B illustrated the medical hologram render a specific view angle with a cut plan to aid visualization of a human body specific area, particularly an aortic valve, an aortic root and a coronary entry point.
Figure 14B:
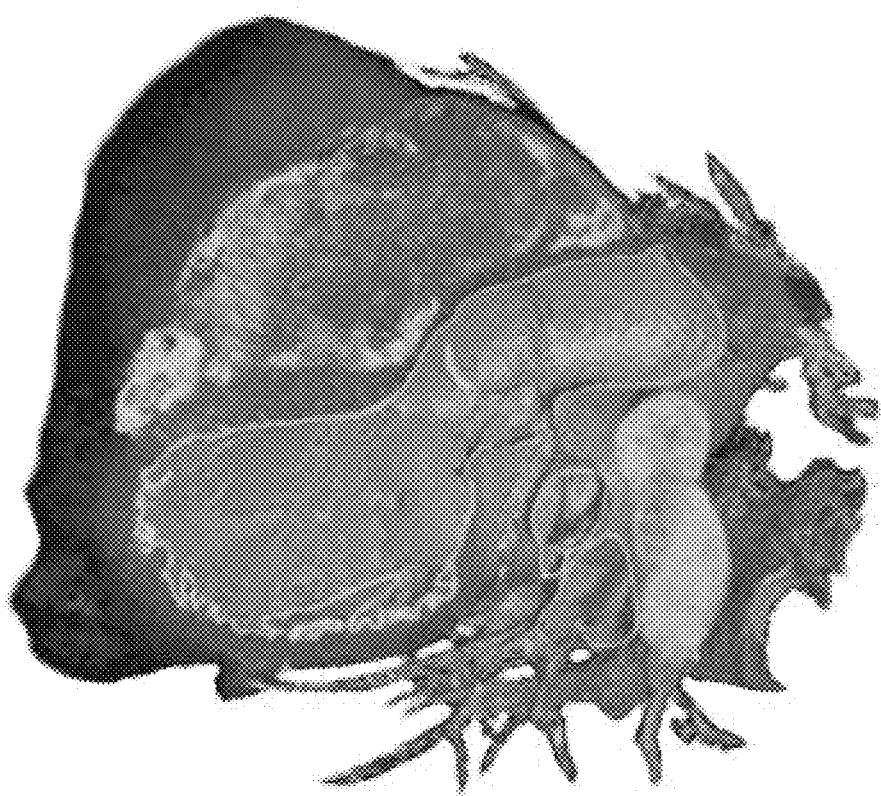

FIG. 14A and FIG. 14B illustrate a medical hologram render using a HOLOPORTAL augmented and mixed reality content creation system using a specific view angle with a cut plan to better visualize a human body specific area such as, in this case, an aortic valve, an aortic root and a coronary entry point.

Figure 15:
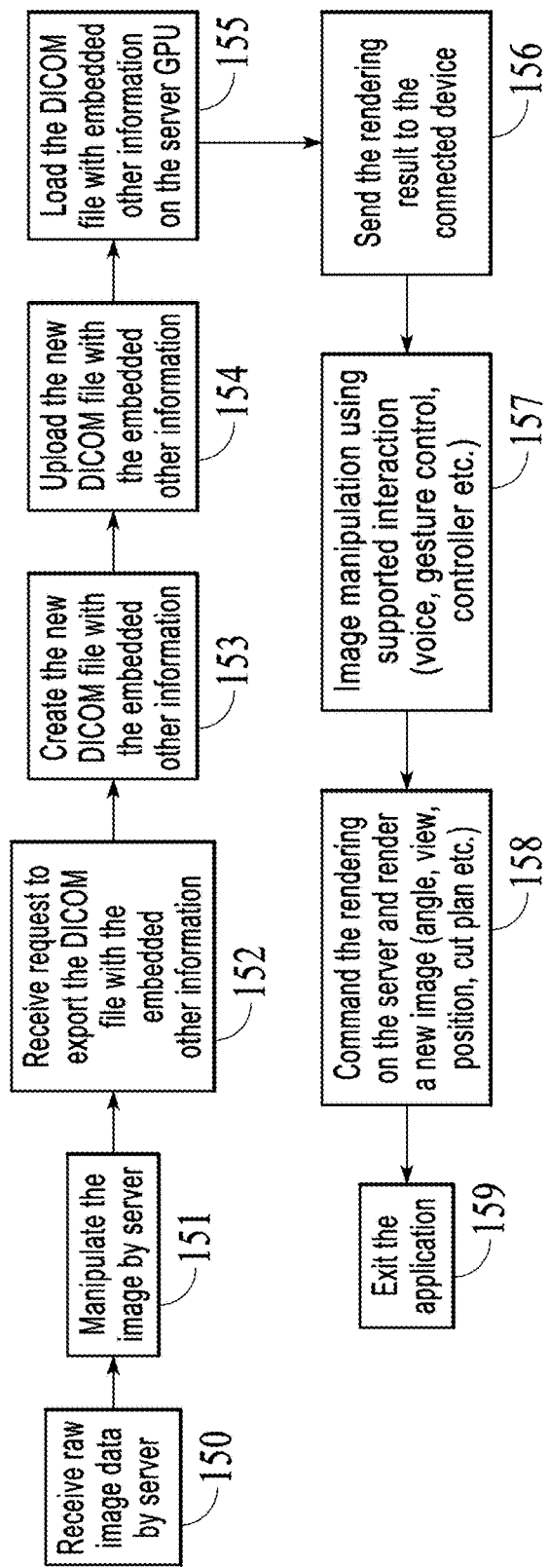
FIG. 15 is a simplified flowchart illustrating hologram creation, hologram loading, client server connection and hologram manipulation between a client and a rendering server.

FIG. 15 describes the hologram creation, loading and client server connection and hologram manipulation between the client and a rendering server. In a block 150, raw image data is received by a server. In a block 151, the image is manipulated by the server. In a block 152, the server receives a request to export the DICOM file with other embedded information. In a block 153, the server creates a new DICOM file with the other embedded information. In a block 154, the new DICOM file with the embedded other information is uploaded. In a block 155, the DICOM file with the embedded other information is loaded on the server graphics processing unit (GPU). In a block 156, the server sends the rendering result to a connected device. In a block 157, a user of a holographic platform application uses an interface on the connected device to perform image manipulation via supported interactions. For example, the supported interactions can include voice commands, gesture control keyboard/mouse control and so on. In a block 158, the server, in response to commands, renders a new image, that includes, for example, changes to one or more of view location, view angle, position, cut plan, and so on. In a block 159, the user exits the holographic platform application.

Figure 16A:
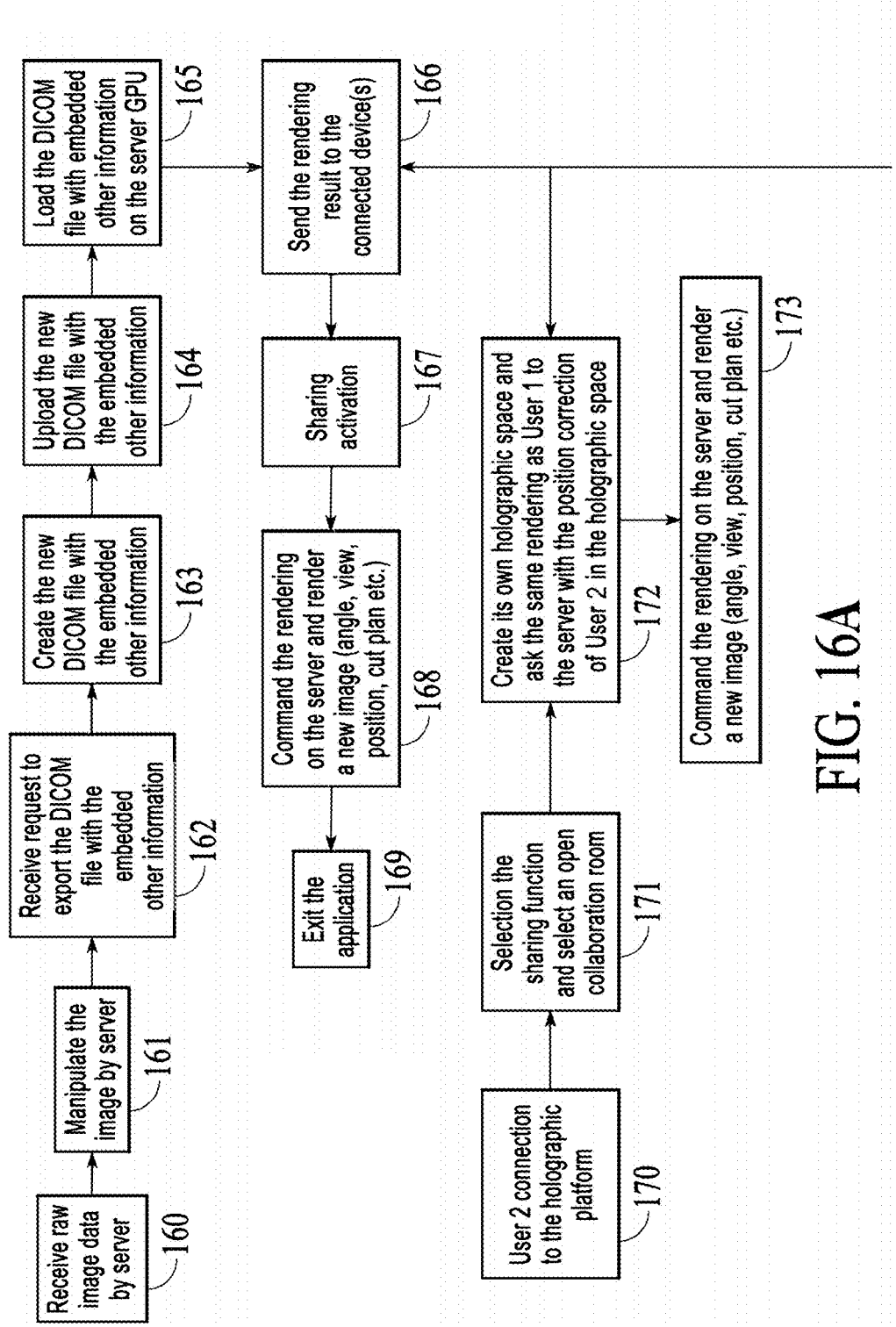
FIG. 16A and FIG. 16B are a simplified flowchart illustrating hologram creation, loading and hologram manipulation between multiple clients and a single rendering server.
Figure 16B:
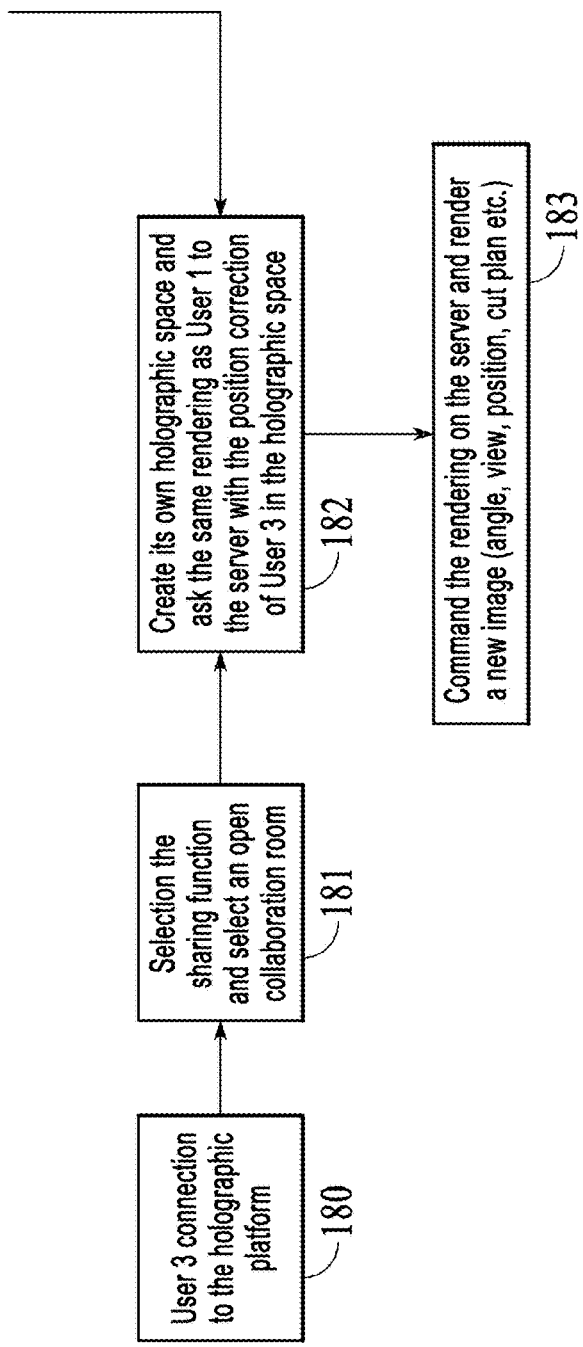

FIG. 16A and FIG. 16B describe the hologram creation, loading and hologram manipulation between multiple clients and one rendering server, in a shared experience configuration. In a block 160, raw image data is received by a server. In a block 161, the image is manipulated by the server. In a block 162, the server receives a request to export the DICOM file with other embedded information. In a block 163, the server creates a new DICOM file with the other embedded information. In a block 164, the new DICOM file with the embedded other information is uploaded. In a block 165, the DICOM file with the embedded other information is loaded on the server graphics processing unit (GPU). In a block 166, the server sends the rendering result to connected devices. In a block 167, a shared activation is performed that allows each authorized user that connects to the holographic platform through a connected device to perform image manipulation via supported interactions. For example, the supported interactions can include voice commands, gesture control keyboard/mouse control and so on. In a block 168, the server, in response to commands from a first user (User 1), renders a new image, that includes, for example, changes to one or more of view location, view angle, position, cut plan, and so on. In a block 169, the user exits the application.

In a block 170 a second user (User 2) of a connected device connects to the holographic platform. In a block 171, the second user selects a sharing function to select an open collaboration room. In a block 172, a second user creates a separate holographic space and requests the same rendering as the first user. For example, the request includes a position correction within holographic space to reflect a virtual position of the second user within the holographic space. In a block 173, the server, in response to commands from the second user renders a new image, that includes, for example, changes to one or more of view location, view angle, position, cut plan, and so on.

In a block 180 a third user (User 3) of a connected device connects to the holographic platform. In a block 181, the third user selects a sharing function to select an open collaboration room. In a block 181, the third user creates a separate holographic space and requests the same rendering as the first user. For example, the request includes a position correction within holographic space to reflect a virtual position of the third user within the holographic space. In a block 183, the server, in response to commands from the third user renders a new image, that includes, for example, changes to one or more of view location, view angle, position, cut plan, and so on.

Figure 17:
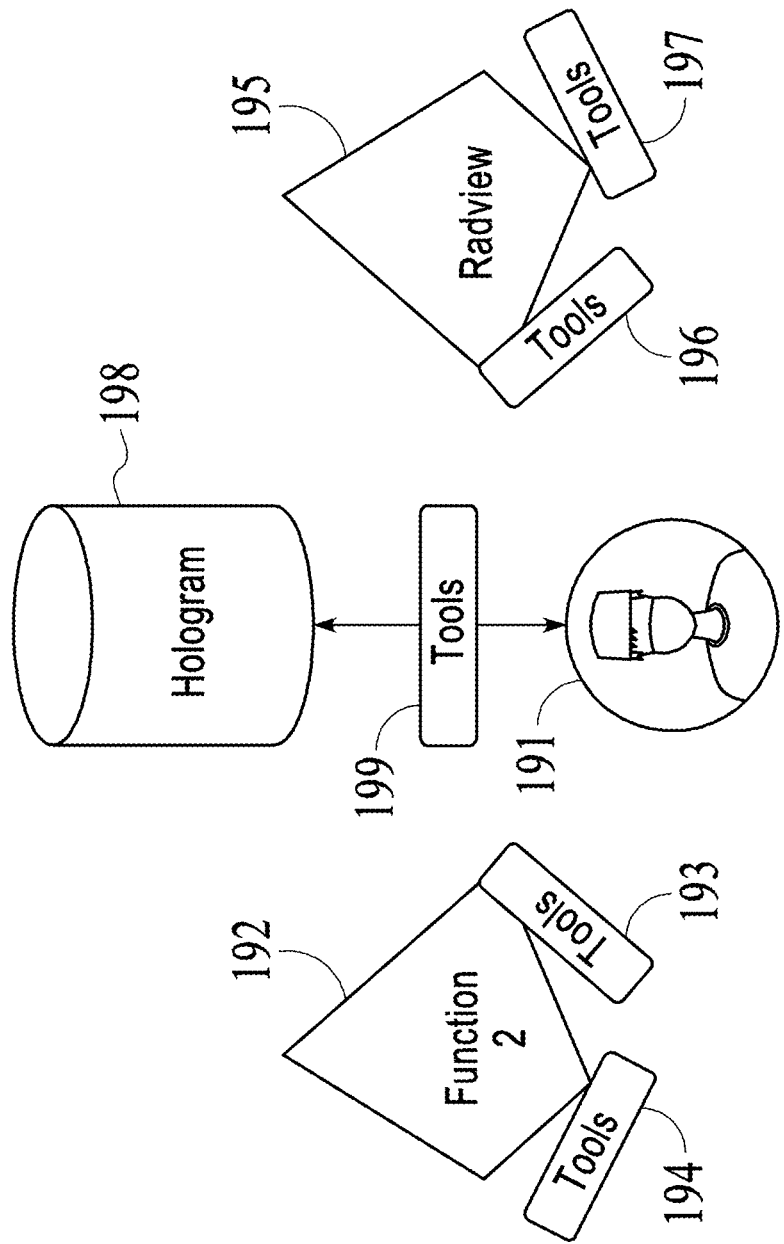
FIG. 17 and FIG. 18 are simplified block diagrams illustrating use of a medical holographic platform
Figure 18:
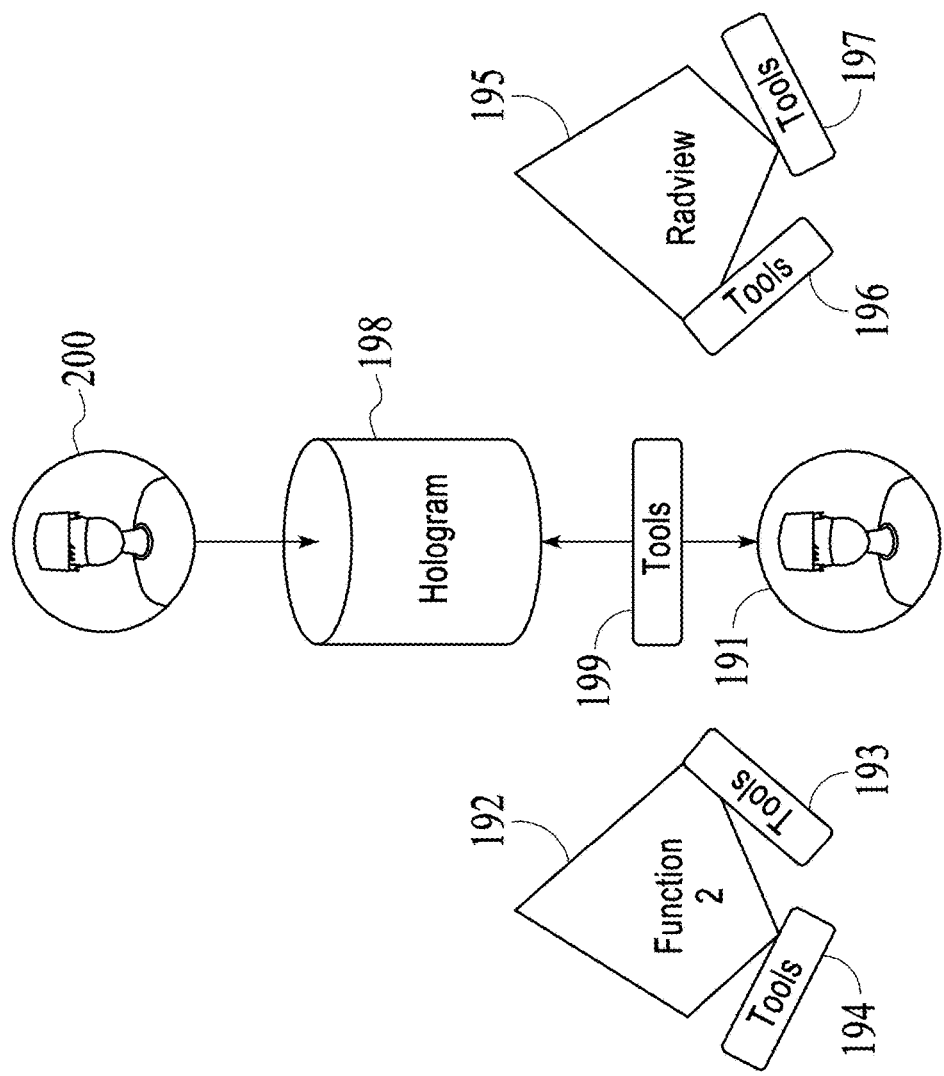

FIG. 17 and FIG. 18 illustrate how a medical holographic platform functions to allow collaboration and sharing.

FIG. 17 illustrates the case where there is only a single user 191. User 191 has available tools 193 to interact with functions 192, and has available tools 196 to use testing and performance monitoring software 195 such as RADVIEW testing and performance monitoring software and the function including collaboration/sharing. User 191 uses tools 199 to interact with a hologram 198 in a holographic display environment. Tools 194 represent other tool sets that can be used by user 191 or other users to interact with functions 192 and tools 197 represent other tool sets that can be used by user 191 or other users for testing and performance monitoring software 195.

FIG. 18 shows that a user 200 has been added as a spectator of hologram 198. User 201 only see hologram 198 and does not control the model. For example, hologram 198 places user 201 in a view location that is the same as the view location for user 191 within hologram 198 and hologram 198 shows user 201 the same view angle that user 191 sees in hologram 198. For example, this spectator configuration can be used to communicate and/or educate healthcare professional and/or medical student and/or patients.

Figure 19:
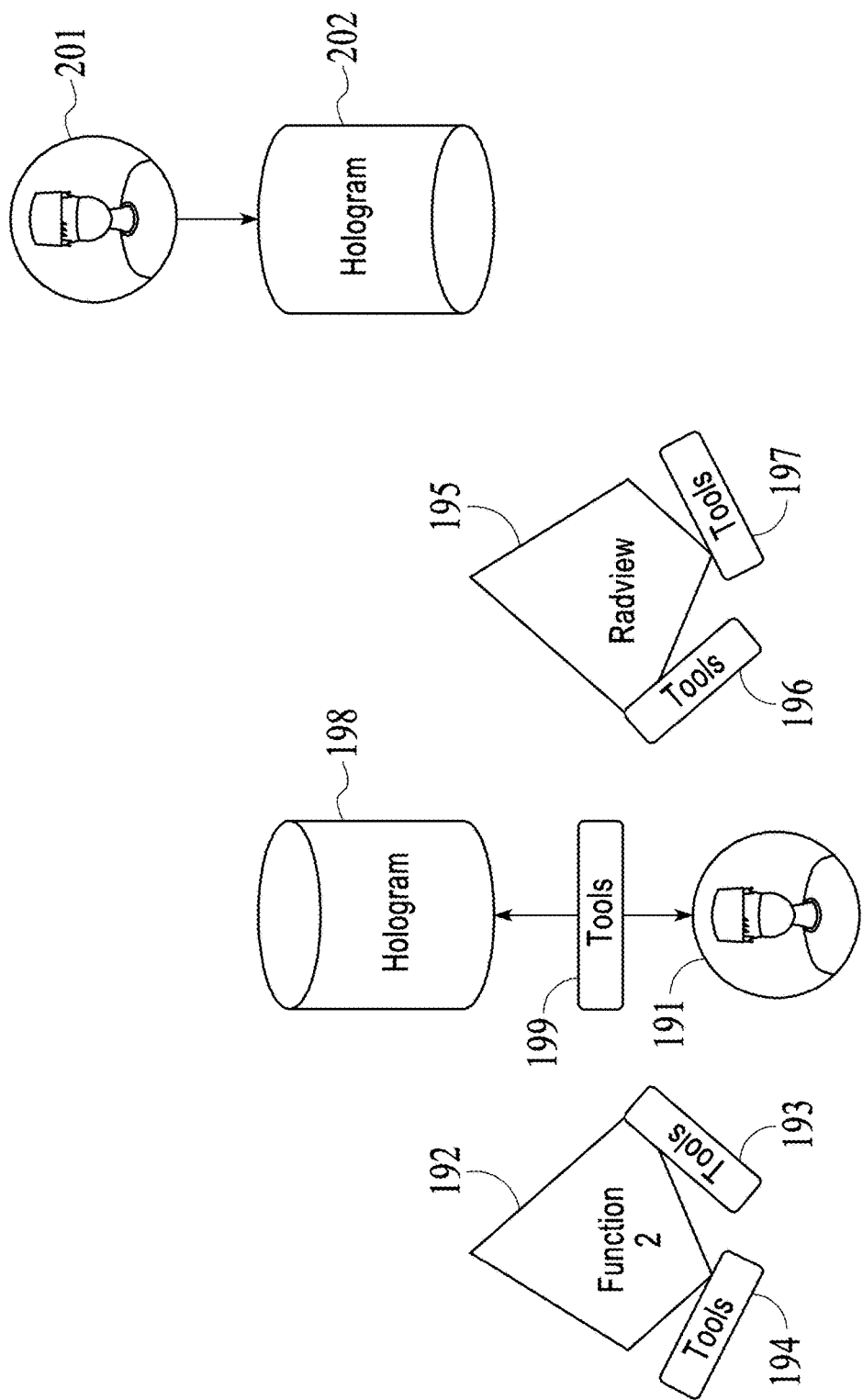
FIG. 19 is a simplified block diagram illustrating a holographic environment with multiple applications.

FIG. 19 shows that a user 201 has been added as a spectator of hologram 202. User 201 only sees hologram 202 and does not control the model. For example, hologram 202 places user 201 in a view location that is different than the view location for user 191 within hologram 198 and hologram 202 shows user 201 a different view angle than user 191 sees in hologram 198. For example, this spectator configuration can also be used to communicate and/or educate healthcare professional and/or medical student and/or patients. In an alternative embodiment, user 201 is able to vary the view location and the view angle seen by user 201.

For example, the application loaded into a holographic space can be 2D application (medical 2D slice manipulation or any other 2D application) or 3D application (medical 3D volume manipulation). The rendering technic used to render the 2D or 3D image can be multiple: VR3D, MIP, MPR, Thick MPR, Thick MIP etc. These rendering technics allows the user to render the model using different method and better illustrated some region of interest which can be better visualized using one or another or a combination of rendering technic.

For example, the medical holographic platform described above can be used as a fundamental layer to ingest medical image or segmented medical viewer, to manipulate a hologram. Additional applications, functions and ensemble of functions can be used to build a specific application focused on a particular clinical area. As illustrated above, such a medical holographic platform allows image manipulation. Additional functions such as real-time hologram registration can be included in the medical holographic platform, for example, to the platform using a specific API.

The medical holographic platform described above includes real time collaboration, which allows users to share a model in real-time in a same physical location and/or different physical location. For example, voice control may be used to control the platform. For example, the medical holographic platform can be used to collaborate between users in different context such as patient education, healthcare professional education, multi-disciplinary expert communication, operating room collaboration, and so on.

The medical holographic platform and architecture allows connection of one or multiple device regardless of the technology used to render the hologram or render a 3D image, augmented reality or virtual reality and regardless of an interface device used. Interface devices can include, for example, a helmet, glasses, a phone, a tablet computing device, a mobile device such as a smart phone, a laptop computing device, a workstation, a diagnostic monitor, multiple monitors and so on.

For example, the medical holographic platform reads a pre-process medical data which contains an automated mask (bone, ribs cage etc.), automated labeling (bone, vessels, organ etc.), automated centerline, (vessels, colon, trachea etc.), and other automated task provided as a result of medical image processing using various types of algorithms such as deterministic and/or artificial intelligence algorithms. The algorithms allow customization of the view of the hologram. The customization can be used, for example, to be focus on a region of interest, to add information to a hologram, to detect some body specificities (vessel, bone etc.) and to apply to specific views.

Figure 20:
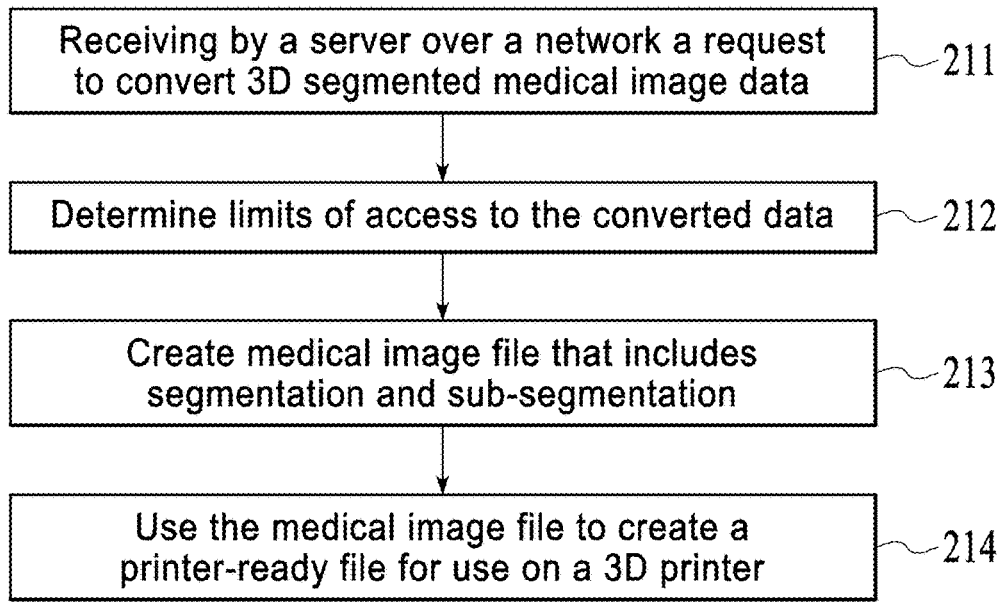
FIG. 20 is a simplified flowchart illustrating an automated 3d printing work flow in accordance with an implementation.

FIG. 20 is a simplified flowchart illustrating an automated 3D printing work flow. In a block 211, a server receives a request to covert a 3D segmented medical image data. For example, the server is a cloud server that receives the request over the Internet or wide area network. Alternatively, the server is a server on a local area network (LAN). For example, the 3D segmented medical image data is from an application running at a client device associated with a user. The segmentation, for example, consists of a multiple sub-segmentation (individual mask) of a particular human anatomy or region of interest. The segmentation will be used to convert the original file containing the medical image data to a print-ready file. The user requests this using medical application that is used to segment the original data.

In a block 212, the limits of access to the converted data are determined. For example, the converted model access (cloud or locally-sited based architecture) is limited to a specific user to process a 3D Printing service request or to access the converted model from the platform established by the server.

In a block 213, a medical image file is created from the medical image data. The medical image file includes the segmentation and sub-segmentation. For example, the medical image file is in a DICOM file format and includes mask segmentation information, color palette, shadowing, transparency, opacity and more of the region of interest from the medical data allowing all this information to be conveniently transferred within a healthcare network. For example, the DICOM images produced on a medical 3D post-processing workstation to be uploaded, viewed, sized and output into a print-ready file that is readable by 3D printers. For example, the DICOM medical image file format embeds information about segmentation of multiple different volumes and sub-volumes of anatomy. The subvolumes may be a particular bone, blood vessel and muscle, and so on. For each volume or subvolume, there is stored, for example, color pallets and lighting (brightness or transparency) information.

In a block 214, the medical image file is used to create a print-ready file for use on a 3D printer. When printed, the resulting 3D physical object represents the exact segmentation and sub-segmentation, including, for example, mask segmentation information, color palette, shadowing, transparency, opacity and the region of interest. For example, the print-ready file is a polygon mesh file supported by a particular destination printer. The format may be a readable PC-format, OBJ, 3MF, STL, FBX, or some other format used by a 3D printer.

Figure 21:
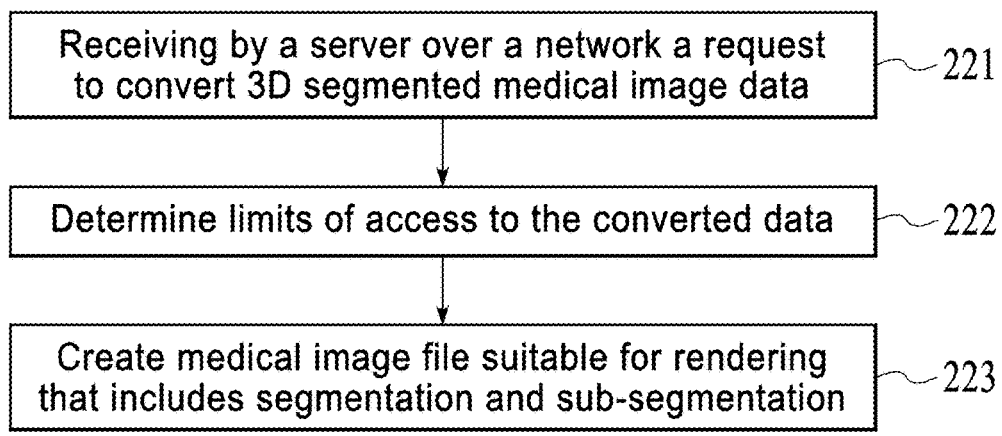
FIG. 21 is a simplified flowchart that illustrates an automated workflow to generate a file in accordance with an implementation.

FIG. 21 is a simplified flowchart that illustrates an automated workflow to generate a file which can be rendered within a holographic platform or rendered in a virtual reality environment. For example, the holographic platform can be run on a device dedicated to holographic viewing, or can be run within a viewing environment by a program that establishes the holographic viewing environment on a general-purpose computing device, such as a personal computer, smartphone or tablet computing device.

In a block 221, a server receives a request to covert a 3D segmented medical image data. For example, the server is a cloud server that receives the request over the Internet or wide area network. Alternatively, the server is a server on a local area network (LAN). For example, the 3D segmented medical image data is from an application running at a client device associated with a user. The segmentation, for example, consists of a multiple sub-segmentation (individual mask) of a particular human anatomy or region of interest. The segmentation will be used to convert the original file containing the medical image data to a holographic-ready file. The user requests this using medical application that is used to segment the original data.

In a block 222, the limits of access to the converted data are determined. For example, the converted model access (cloud or locally-sited based architecture) is limited to a specific user to render the hologram or 3D model into a holographic or virtual reality platform. For example, holographic or virtual reality platform runs on a device devoted to displaying holographic or virtual reality or runs as an application on a general-purpose computing device, such as a personal computer, smartphone or tablet computing device.

In a block 223, a medical image file is created from the medical image data. The medical image file includes the segmentation and sub-segmentation. For example, the segmentation and sub-segmentation includes mask segmentation information, color palette, shadowing, transparency, opacity and the region of interest from the medical data allowing all this information to be conveniently transferred within a healthcare network.

Figure 22:
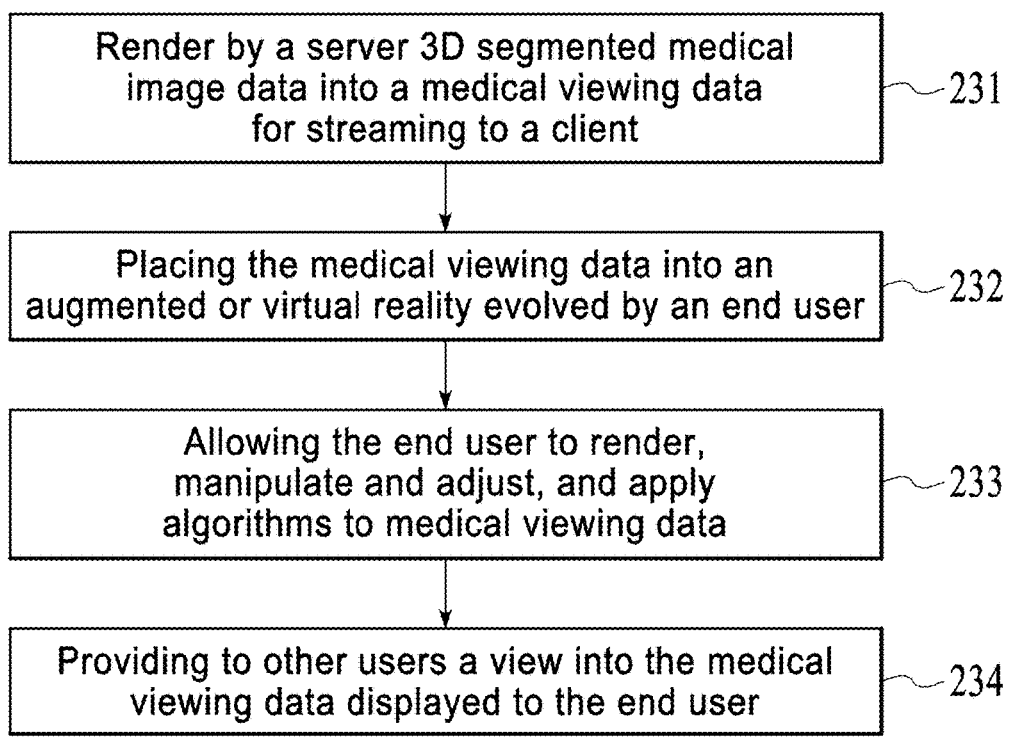
FIG. 22 is a simplified flowchart that illustrates multiple person viewing of rendered medical images in accordance with an implementation.

FIG. 22 is a simplified flowchart that illustrates multiple person viewing of rendered medical images. In a block 231 a server renders 3D segmented medical image data into medical viewing data for streaming to a client system. For example, the server is a cloud server that receives the request over the Internet or wide area network. Alternatively, the server is a server on a local area network (LAN). For example, the 3D segmented medical image data is from an application running at a client device associated with a user. The segmentation, for example, consists of a multiple sub-segmentation (individual mask) of a particular human anatomy or region of interest. The segmentation consists of a multiple sub-segmentation of individual segmentation masks of a particular human anatomy or region of interest. For example, the server renders medical image in its raw format (e.g., the DICOM medical data format) to stream to the client. For example, the client is a holographic device such as a HoloLens™ headset, or a holographic platform running on a mobile device such as a smartphone, tablet computing device, laptop computer, and so on and/or virtual reality device. For example, the server rendering allows rendering without any file size limit and in an original format as acquired by an imaging device or devices such as a CT scanner and or an MRI device.

In a block 232, the medical viewing data as rendered is placed into an augmented reality environment and/or virtual reality environment. Alternatively, or in addition, the medical viewing data is rendered and viewed by a specialized medical viewer. For example, the medical viewer includes specialized medical applications and functions, including, for example, use of augmented reality and/or virtual reality.

In a block 233, the end-user to render, manipulate, adjust, the rendered medical viewing data and apply algorithms for the rendering. The data as viewed may be, for example one or a combination of 3D rendered data, a hologram, image data formatted for viewing on a special medical image viewing device.

In a block 234, other users are provided a view into the medical viewed data displayed to the end user. For example, one or several other users are allowed to see on their own viewing devices, in real-time what the end user view sees. This includes, for example, the same holographic or virtual environment including its loaded element. For example, a medical image viewer is placed into a virtual viewing area that includes with synchronization of the settings and orientation of the original medical image data used to create the augmented reality volumetric anatomic object being simultaneously viewed in the same augmented reality glasses. Or similarly viewed with another device such as a PC monitor, mobile device or other viewing device or combination thereof.

The shared holographic environment or virtual environment can be manipulated and shared by the end user, allowing discussion with other users about, for example, the loaded application, loaded images, loaded 3D rendering and so on. The sharing environment can include a representation of each user as a real 4D capture of each user or 3D representation of them.

Alternatively, or in addition, several users on different user devices are able to establish different viewer locations in a spectator configuration, as discussed above, the different viewer locations include, for example, placing the viewers at a view location that is different than the view location for end user, including a different view angle than is seen by the end user.

For example, a user on medical image viewer is virtually placed into the virtual viewing area. There is synchronization of settings and orientation of the original medical image data used to create the augmented reality volumetric anatomic object being simultaneously viewed in the same type of medical image viewer. For example, each medical image viewer includes augmented reality glasses. Also, similarly for virtual reality, viewing on PC monitors, mobile device or other viewing device or combination thereof may be used.

The foregoing discussion discloses and describes merely exemplary methods and implementations. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

What is claimed is:

1. A method that allows multiple person viewing of rendered medical image, the method comprising:
    receiving, by a server, medical image data;
    manipulating the medical image data by the server to produce first rendered medical image data that includes the medical image data plus image manipulation results;
    sending the first rendered medical image data to a first client system;
    displaying, to the first end user on the first client system, a first 3-D medical image that is based on the first rendered medical image data, the first 3-D medical image being displayed within an augmented reality environment or a virtual reality environment so that within the augmented reality environment or the virtual reality environment the first end user has a first viewer location and a first viewing angle of the first 3-D medical image;
    in response to instructions from the first end user, additionally manipulating the medical image data by the server to produce second rendered medical image data that includes the medical image data plus results of the additional image manipulation;
    sending the second rendered medical image data to the first client system;
    displaying, to the first end user on the first client system, a second 3-D medical image that is based on the second rendered medical image data, the second 3-D medical image being displayed within the augmented reality environment or the virtual reality environment so that within the augmented reality environment or the virtual reality environment the first end user has at least one of a second viewer location and a second viewing angle that is different from at least one of the first viewer location and the first viewing angle of the first 3-D medical image;
    in response to connection of a second end user, additionally manipulating the medical image data by the server to produce third rendered medical image data that includes the medical image data plus results of additional image manipulation; and,
    displaying, to the second end user, a third 3-D medical image that is based on the third rendered medical image data, the third 3-D medical image being displayed within the augmented reality environment or the virtual reality environment so that within the augmented reality environment or the virtual reality environment the second end user has at least one of a third viewer location and a third viewing angle that is different from at least one of the first viewer location and the first viewing angle of the first 3-D medical image.

2. A method as in claim 1, wherein the medical image data is digital imaging and communications in medicine (DICOM) compatible data.

3. A method as in claim 1, wherein the second user is on a second client system.

4. A method as in claim 1, wherein the second user is on the first client system and views the third 3-D medical image in a display that is different a display on which the first user views the first 3-D medical image and the second 3-D image.

5. A method as in claim 1, wherein manipulating the medical image data by the server includes:
    converting the medical image data from digital imaging and communications in medicine (DICOM) compatible data to another image data format when producing the first rendered medical image.

6. A method as in claim 5, wherein manipulating the medical image data by the server includes:
    converting the medical image data from digital imaging and communications in medicine (DICOM) compatible data to a converted data format, wherein the converted data format allows multiple sub-segmentation of a particular human anatomy or region of interest, and wherein the converted data format allows for storing mask segmentation information, color palette, shadowing, transparency and opacity.

7. A method as in claim 5, wherein manipulating the medical image data by the server includes:
    converting the medical image data to a converted data format, wherein the converted data format allows multiple sub-segmentation of a particular human anatomy or region of interest, and wherein the converted data format allows for storing mask segmentation information, color palette, shadowing, transparency and opacity.

8. A method as in claim 7 wherein the converted file format is a digital imaging and communications in medicine (DICOM) file format.

9. A method as in claim 1, additionally comprising:
    in response to connection of a third end user, additionally manipulating the medical image data by the server to produce fourth rendered medical image data that includes the medical image data plus results of additional image manipulation; and,
    displaying, to the third end user, a fourth 3-D medical image that is based on the fourth rendered medical image data, the fourth 3-D medical image being displayed within the augmented reality environment or the virtual reality environment so that within the augmented reality environment or the virtual reality environment the third end user has at least one of a fourth viewer location and a fourth viewing angle that is different from at least one of the first viewer location and the first viewing angle of the first 3-D medical image.

10. A method that allows multiple person viewing of rendered medical image, the method comprising:
    receiving, by a server, medical image data;
    manipulating the medical image data by the server to produce first rendered medical image data that includes the medical image data plus image manipulation results;

sending the first rendered medical image data to a first client system;

displaying, to the first end user on the first client system, a first 3-D medical image that is based on the first rendered medical image data, the first 3-D medical image being displayed within an augmented reality environment or a virtual reality environment so that within the augmented reality environment or the virtual reality environment the first end user has a first viewer location and a first viewing angle of the first 3-D medical image;

in response to connection of a second end user, additionally manipulating the medical image data by the server to produce second rendered medical image data that includes the medical image data plus results of additional image manipulation; and, displaying, to the second end user, a second 3-D medical image that is based on the second rendered medical image data, the second 3-D medical image being displayed within the augmented reality environment or the virtual reality environment so that within the augmented reality environment or the virtual reality environment the second end user has at least one of a second viewer location and a second viewing angle that is different from at least one of the first viewer location and the first viewing angle of the first 3-D medical image.

11. A method as in claim 10, additionally comprising:
in response to instructions from the first end user, additionally manipulating the medical image data by the server to produce third rendered medical image data that includes the medical image data plus results of the additional image manipulation;
sending the third rendered medical image data to the first client system;
displaying, to the first end user on the first client system, a third 3-D medical image that is based on the third rendered medical image data, the third 3-D medical image being displayed within the augmented reality environment or the virtual reality environment so that within the augmented reality environment or the virtual reality environment the first end user has at least one of a third viewer location and a third viewing angle that is different from at least one of the first viewer location and the first viewing angle of the first 3-D medical image.

12. A method as in claim 10, wherein the medical image data is digital imaging and communications in medicine (DICOM) compatible data.

13. A method as in claim 10, wherein the second user is on a second client system.

14. A method as in claim 10, wherein the second user is on the first client system and views the second 3-D medical image in a display that is different a display on which the first user views the first 3-D medical image and the second 3-D image.

15. A method as in claim 10, wherein manipulating the medical image data by the server includes:
converting the medical image data from digital imaging and communications in medicine (DICOM) compatible data to another image data format when producing the first rendered medical image.

16. A method as in claim 15, wherein manipulating the medical image data by the server includes:
converting the medical image data from digital imaging and communications in medicine (DICOM) compatible data to a converted data format, wherein the converted data format allows multiple sub-segmentation of a particular human anatomy or region of interest, and wherein the converted data format allows for storing mask segmentation information, color palette, shadowing, transparency and opacity.

17. A method as in claim 15, wherein manipulating the medical image data by the server includes:
converting the medical image data to a converted data format, wherein the converted data format allows multiple sub-segmentation of a particular human anatomy or region of interest, and wherein the converted data format allows for storing mask segmentation information, color palette, shadowing, transparency and opacity.

18. A method as in claim 17 wherein the converted file format is a digital imaging and communications in medicine (DICOM) file format.

19. A method as in claim 10, additionally comprising:
in response to connection of a third end user, additionally manipulating the medical image data by the server to produce third rendered medical image data that includes the medical image data plus results of additional image manipulation; and,
displaying, to the third end user, a third 3-D medical image that is based on the third rendered medical image data, the third 3-D medical image being displayed within the augmented reality environment or the virtual reality environment so that within the augmented reality environment or the virtual reality environment the third end user has at least one of a third viewer location and a third viewing angle that is different from at least one of the first viewer location and the first viewing angle of the first 3-D medical image.

20. A method that allows multiple person viewing of rendered medical image, the method comprising:
receiving a medical image data;
manipulating the medical image data to produce first rendered medical image data that includes the medical image data plus image manipulation results;
displaying, to the first end user on a first display, a first 3-D medical image that is based on the first rendered medical image data, the first 3-D medical image being displayed within an augmented reality environment or a virtual reality environment so that within the augmented reality environment or the virtual reality environment the first end user has a first viewer location and a first viewing angle of the first 3-D medical image;
in response to instructions from the first end user, additionally manipulating the medical image data to produce second rendered medical image data that includes the medical image data plus results of the additional image manipulation;
displaying, to the first end user on the first display, a second 3-D medical image that is based on the second rendered medical image data, the second 3-D medical image being displayed within the augmented reality environment or the virtual reality environment so that within the augmented reality environment or the virtual reality environment the first end user has at least one of a second viewer location and a second viewing angle that is different from at least one of the first viewer location and the first viewing angle of the first 3-D medical image;
in response to connection of a second end user, additionally manipulating the medical image data by the server to produce third rendered medical image data that includes the medical image data plus results of additional image manipulation; and, displaying, to the second end user on a second display, a third 3-D medical image that is based on the third rendered medical image data, the third 3-D medical image being displayed within the augmented reality environment or the virtual reality environment so that within the augmented reality environment or the virtual reality environment the second end user has at least one of a third viewer location and a third viewing angle that is different from at least one of the first viewer location and the first viewing angle of the first 3-D medical image.

* * * * *